(12) United States Patent
Xu et al.

(10) Patent No.: US 10,508,092 B2
(45) Date of Patent: Dec. 17, 2019

(54) SYNTHESIS OF NOVEL ANALOGS OF DIPTOINDONESIN G, COMPOUNDS FORMED THEREBY, AND PHARMACEUTICAL COMPOSITIONS CONTAINING THEM

(71) Applicant: Wisconsin Alumni Research Foundation, Madison, WI (US)

(72) Inventors: Wei Xu, Middleton, WI (US); Weiping Tang, Middleton, WI (US); Jitian Liu, Madison, WI (US); Jill Kolesar, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 9 days.

(21) Appl. No.: 15/689,378

(22) Filed: Aug. 29, 2017

(65) Prior Publication Data
US 2018/0065945 A1     Mar. 8, 2018

Related U.S. Application Data

(60) Provisional application No. 62/382,987, filed on Sep. 2, 2016.

(51) Int. Cl.
*C07D 307/79*     (2006.01)
*C07D 307/77*     (2006.01)

(52) U.S. Cl.
CPC ......... *C07D 307/79* (2013.01); *C07D 307/77* (2013.01)

(58) Field of Classification Search
None
See application file for complete search history.

(56) References Cited

PUBLICATIONS

Kim, K. et al., Org. Lett. 2010 vol. 12, pp. 5314-5317.*
Sarma, S. et al., J. Org. Chem.(2010), 75(11), 3806-3813.*
CAPLUS 1934 28584.*
Arai, S et al., Bull Chem Soc Jap 1991 vol. 64 pp. 324-326.*
Liu, J. et al., Org Biomol Chem 2016 vol. 14 pp. 8927-8930.*
Al-Dhaheri et al. (2011) "CARM1 Is an Important Determinant of ERα-Dependent Breast Cancer Cell Differentiation and Proliferation in Breast Cancer Cells," *Cancer research* 71:2118-2128.

Chauhan et al., "Synthesis of novel benzo[b]thiophenes: analogs of combretastatin and resveratrol," *Heterocycl. Commun.*, 2010, 16, 241.
Covaleda et al., "Influence of Cellular ERα/Erβ Ratio on the ERα-Agonist Induced Proliferation of Human T47D Breast Cancer Cells," *Toxicol. Sci.*, 2008, 105, 303.
Ge et al., "Immunosuppressive Resveratrol Aneuploids from *Hopea chinensis*," Tan, *Chem. Eur. J.*, 2010, 16, 6338.
Greene, Theodora W. "Protective Groups in Organic Synthesis," (John Wiley & Sons, Inc., New York, 1991, ISBN 0-471-62301-6 (Book—Copy Not Provided).
Greene's Protective Groups in Organic Synthesis, ISBN-13: 978-1118057483, © 2014, John Wiley & Sons, Inc., 5th Edition, Chapter 1, Protecting Groups: An Overview, Chapter 2, Hydroxyl Protecting Groups, Chapter 4, Carboxyl Protecting Groups, and Chapter 5, Carbonyl Protecting Groups (Book—Copy Not Provided).
Hamilton et al., "benzofuranyl 3,5-bis-Polyamine Derivatives as Time-Dependent Inhibitors of Trypanothione Reductase," *Bioorg. Med. Chem.*, 2003, 11, 3683.
Hung et al., "Site-selective Suzuki cross-coupling reactions of 2,3-dibromebenzofuran," *Tetrahedron Lett.*, 2010, 51, 2420.
Hussain et al., "Efficient synthesis of functionalized dibenzofurans by domino 'twofold Heck/6π-electrocyclization' reactions of 2,3-di- and 2,3,5-tribromobenzofuran," *Tetrahedron Lett.*, 2009, 50, 3929.
Hussain et al., Synthesis of Arylated Benzofurans by Regioselective Suzuki-Miyaura Cross-Coupling Reactions of 2,3-Dibromobenzofurans- and 2,3,5-Tribromobenzofurans, « *J. Heterocycl. Chem.*, 2015, 52, 497.
Jeselsohn et al. (2014) "Emergence of constitutively active estrogen receptor-alpha mutations in pretreated advanced estrogen receptor-positive breast cancer," *Clinical cancer research: an official journal of the American Association for Cancer Research*, 20:1757-1767.
Juliawaty et al., "A 2-Arylbenzofuran Derivative From Hopea Mengarawan," *Nat. Prod. Commun.*, 2009, 4, 947.
Kim et al., "BCl$_3$-promoted synthesis of benzofurans," *Tetrahedron Lett.*, 2008, 49, 6579.
Kim et al., "A versatile approach to oligostilbenoid natural products—synthesis of permethylated analogues of viniferifuran, malibatol A, and shoreaphenol," *Org. Lett.*, 2010, 12, 5314.
Kim et al., "Total Synthesis of Diptoindonesin G via a Highly Efficient Domino Cyclodehydration/Intramolecular Friedel-Crafts Acylation/Regioselective Demethylation Sequence," *Org. Biomol. Chem.*, 2009, 7, 2788.
Lee et al., "Palladium-Catalyzed α-Arylation of Aryloxyketones for the Synthesis of 2,3-Disubstituted Nezofurans," *J. Org. Chem.*, 2014, 79, 6153.
Lu et al., "Synthesis of Internal Alkynes through the Pd-Catalyzed Coupling of Heteroaryl Halides with Terminal Alkynes," *Eur. J. Org. Chem.*, 2013, 2013, 1644.

(Continued)

*Primary Examiner* — Heidi Reese
(74) *Attorney, Agent, or Firm* — Joseph T. Leone, Esq.; DeWitt LLP

(57) ABSTRACT

Disclosed are unnatural analogs of Diptoindonesin G, methods to make the analogs, pharmaceutical compositions containing the analogs, and methods of using the analogs to inhibit neoplastic cell growth.

31 Claims, 6 Drawing Sheets

(56) References Cited

PUBLICATIONS

McCormack et al., (2008) "Pharmacokinetic profile of the fulvestrant loading dose regimen in postmenopausal women with hormone receptor-positive advanced breast cancer," *Clinical breast cancer* 8:347-351.

Merenbakh-Lamin et al. (2013) "D538G mutation in estrogen receptor-alpha: A novel mechanism for acquired endocrine Resistance in breast cancer," *Cancer research*, 73:6856-6864.

Pritchard et al. (2010) "Results of a phase II study comparing three dosing regimens of fulvestrant in postmenopausal women with advanced breast cancer (FINDER2)," *Breast cancer research and treatment* 123:453-461.

Saitoh et al, "2-{3-[4-(Alkylsufinyl)phenyl]-l-benzofuran-5-yl}-5-methyly-1,3,4-oxadiazole Derivatives as Novel Inhibitors of Glycogen Synthase Kinase-3β with Good Brain Permeability," *J. Med. Chem.*, 2009, 52, 6270.

Salman et al., "Pyrrole versus quinoline formation in the palladium catalyzed reaction of 2-alkynyl-3-bromothiophenes and 2-alkynyl-3-bromofurans with anilines. A combined experimental and computational study," *Org. Biomol. Chem.*, 2012, 10, 9464.

Scott et al. (2016) "ERpS294 is a biomarker of ligand or mutational ERα activation and a breast cancer target for CDK2 inhibition," Oncotarget, DOI: 10.18632/oncotarget.12735.

Sista et al., "Synthesis and Optoelectronic Properties of Novel Benzodifuran Semiconducting Polymers," *J. Polym. Sci., Part A: Polym. Chem.*, 2012, 50, 4316.

Wang et al., (2014) "CARM1 methylates chromatin remodeling factor BAF155 to enhance tumor progression and metastasis," *Cancer Cell* 25:21-36.

Wardell et al. (2015) "Efficacy of SERD/SERM Hybrid-CDK4/6 Inhibitor Combinations in Models of Endocrine Therapy-Resistant Breast Cancer," *Clin Cancer Res.* 21(22):5121-5130.

Zhao et al., "Reciprocal Regulation of ERα and ERβ Stability and Activity by Diptoindonesin G," *Chem. Biol.*, 2015, 22, 1608.

\* cited by examiner

SYNTHESIS OF NOVEL ANALOGS OF DIPTOINDONESIN G, COMPOUNDS FORMED THEREBY, AND PHARMACEUTICAL COMPOSITIONS CONTAINING THEM

CROSS-REFERENCE TO RELATED APPLICATIONS

Priority is hereby claimed to provisional application Ser. No. 62/382,987, filed Sep. 2, 2016, which is incorporated herein by reference.

FEDERAL FUNDING STATEMENT

This invention was made with government support under W81XWH-11-1-0237 awarded by the US ARMY/MRMC. The government has certain rights in the invention.

BACKGROUND

Natural product diptoindonesin (Dip) G 1 was isolated from tree barks of *Hopea mengarawan* in Indonesia together with nine other oligostilbenoids in 2009. (L. D. Juliawaty, Sahidin, E. H. Hakim, S. A. Achmad, Y. M. Syah, J. Latip and I. M. Said, *Nat. Prod. Commun.*, 2009, 4, 947.) Around the same time, the same molecule was also isolated from *Hopea chinensis* stem barks in China. (H. M. Ge, W. H. Yang, Y. Shen, N. Jiang, Z. K. Guo, Q. Luo, Q. Xu, J. Ma and R. X. Tan, *Chem. Eur. J.*, 2010, 16, 6338.) Dip G has a tetracyclic core with A-D rings bearing a ketone and three phenolic OH groups and an additional E-ring with one more phenolic OH group. Dip G showed anti-proliferation effect in murine leukemia P-388 cells (Juliawaty et al., supra) and immunosuppressant activity in a concanavalin A induced proliferation of mouse splenic lymphocytes (T cells) assay. (Ge et al., supra.) Recently, it was reported that Dip G could regulate the stability of estrogen receptor α (ERα) and estrogen receptor β (ERβ), two members of the steroid nuclear receptor superfamily with opposing effect on cell proliferation. (Z. Zhao, L. Wang, T. James, Y. Jung, I. Kim, R. Tan, F. M. Hoffmann and W. Xu, *Chem. Biol.*, 2015, 22, 1608.) ERα promotes cell proliferation, while ERβ has an anti-proliferative effect in breast cancer cells. (A. M. S. Covaleda, H. Van den Berg, J. Vervoort, P. Van der Saag, A. Strom, J.-A. Gustafsson, I. Rietjens and A. J. Murk, *Toxicol. Sci.*, 2008, 105, 303.) Interestingly, Dip G decreases the stability of the oncogenic ERα and increases the stability of ERβ, a tumor suppressor in breast cancer. Instead of directly interacting with ERs, Dip G was found to target the E3 ubiquitin ligase C-terminus of HSC70-interacting protein (CHIP), also known as STIP1 homology and U-Box containing protein 1 (STUB1). (Zhao et al, supra.)

The only total synthesis of Dip G to date was reported by Kim and Kim in 2010, K. Kim and I. Kim, *Org. Lett.*, 2010, 12, 5314.

SUMMARY

Disclosed herein are compounds selected from the group consisting of:

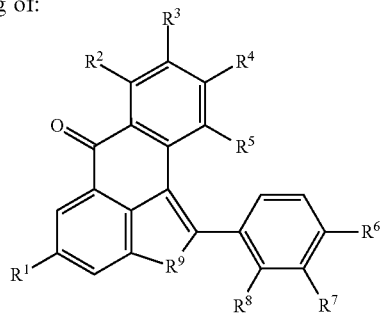

wherein $R^1$, $R^2$, $R^3$, $R^4$, $R^5$, $R^6$, $R^7$, and $R^8$ are independently selected from the group consisting of —H, —OH, —OR$^{10}$, —NH$_2$, —NHR$^{10}$, and —NR$^{10}$R$^{11}$, wherein $R^{10}$ and $R^{11}$ are independently selected from the group consisting of $C_1$-$C_6$-alkyl, provided that $R^1$, $R^2$, $R^4$, and $R^6$ are not simultaneously —OH; $R^9$ is —O—, —NH—, or —S—; and salts thereof. The salts may be pharmaceutically suitable salts.

Specifically disclosed herein are compounds as described above wherein $R^9$ is —O—

Also disclosed herein are compounds as described above wherein $R^1$ is —H. $R^2$ is —H, or $R^3$ is —H, or $R^4$ is —H, or $R^5$ is —H, or $R^6$ is —H, or $R^7$ is —H, or $R^8$ is —H, or $R^1$ is —OH, or $R^2$ is —OH, or $R^3$ is —OH, or $R^4$ is —OH, or $R^5$ is —OH, or $R^6$ is —OH, or $R^7$ is —OH, or $R^8$ is —OH, or $R^1$ and $R^2$ are —H, or $R^1$ and $R^4$ are —H, or $R^1$ and $R^6$ are —H, or $R^2$ and $R^4$ are —H, or $R^2$ and $R^6$ are —H, or $R^4$ and $R^6$ are —H.

Compounds disclosed herein include various positional isomers, such as (but not limited to):

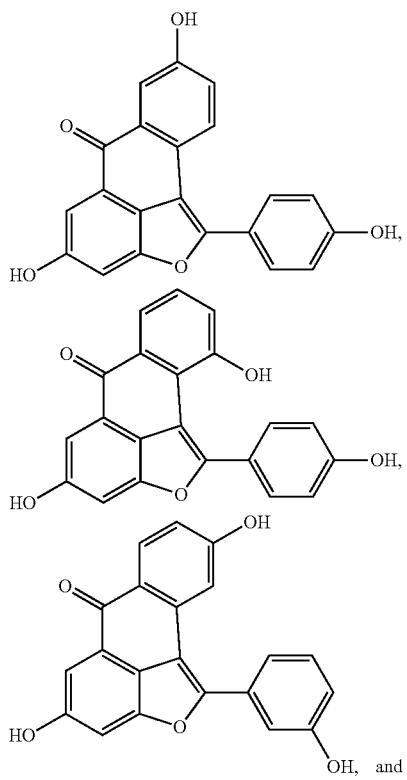

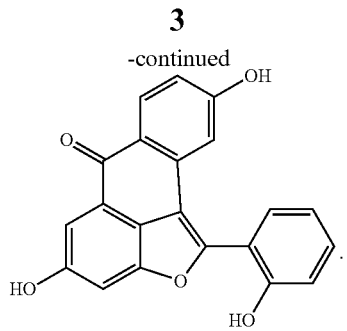

Also disclosed herein are pharmaceutical compositions comprising an amount of a compound as recited any of the preceding paragraphs, in combination with a pharmaceutically suitable delivery vehicle.

Further disclosed herein is a method of inhibiting neoplastic cell growth, the method comprising contacting a neoplastic cell or a cell suspected of being neoplastic with a growth inhibiting-effective amount of a compound as recited in any of the preceding paragraphs.

Still further disclosed herein is a method of making diptoindonesin G and analogs thereof, the method comprising the following reaction sequence:

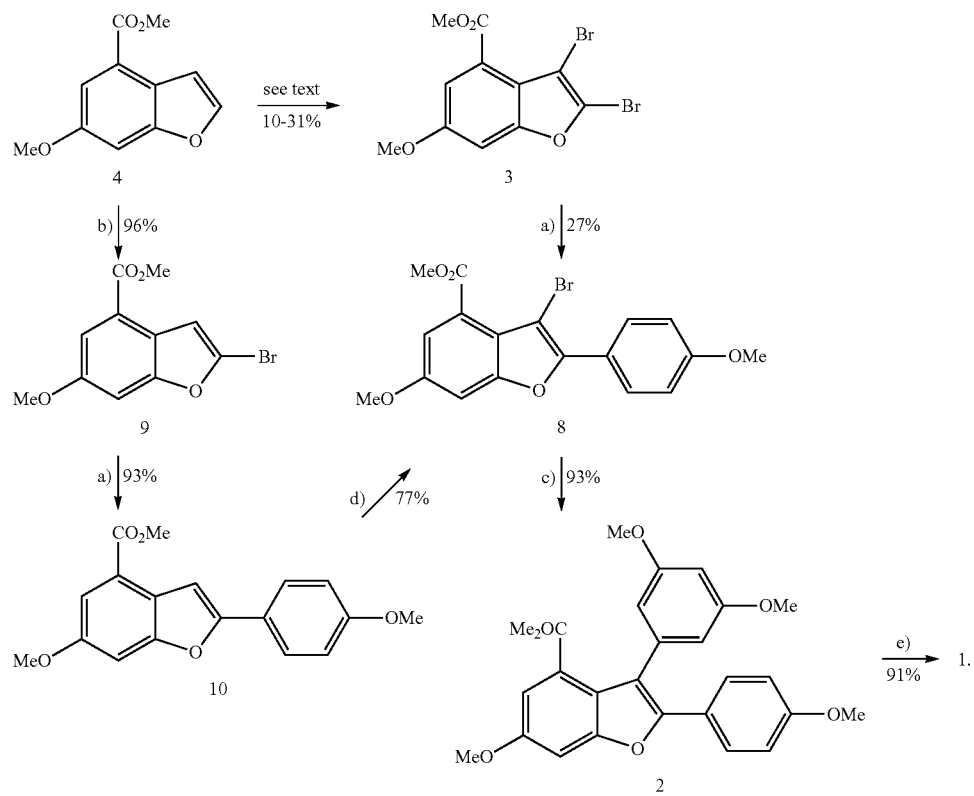

Also disclosed herein is a method of making analogs of diptoindonesin G, the method comprising the following reaction sequence:

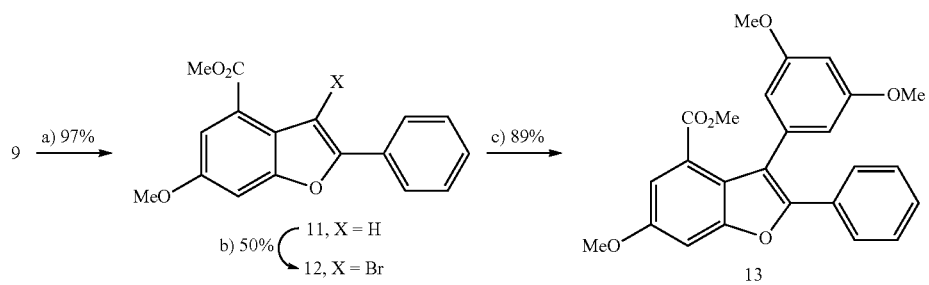

-continued

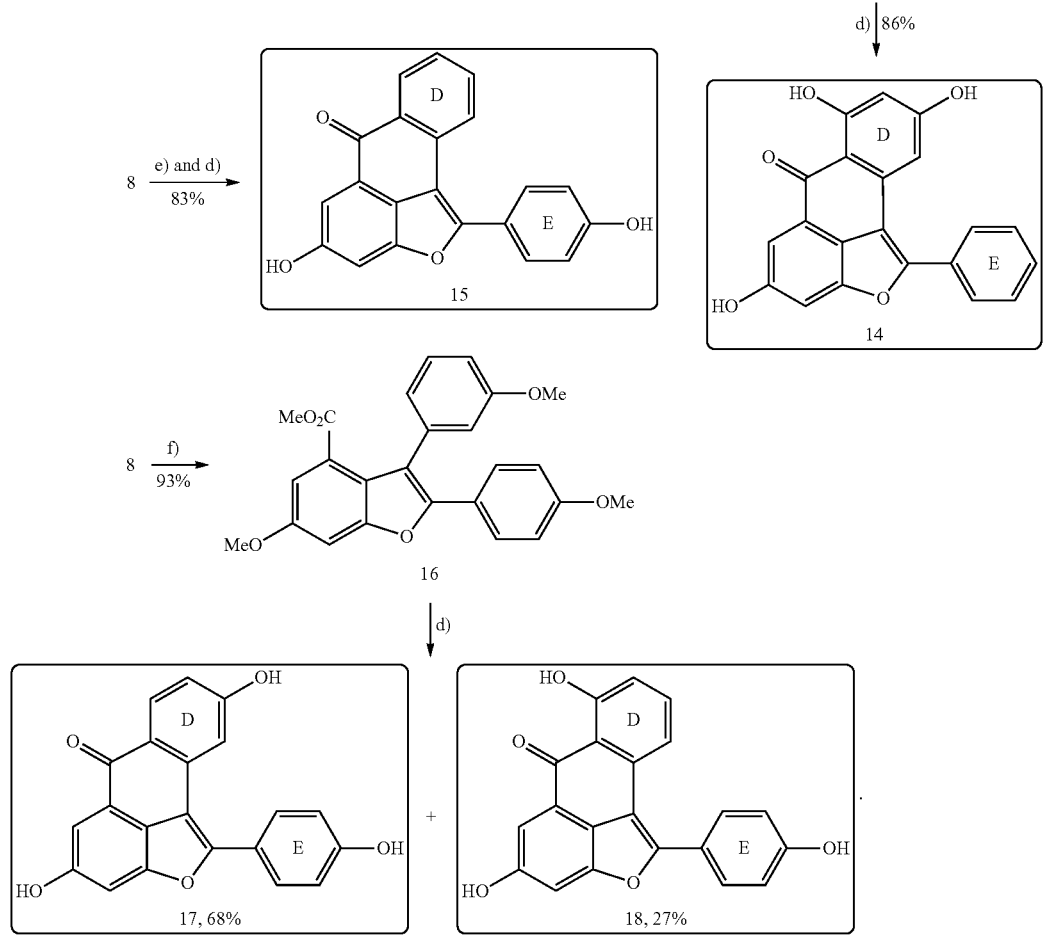

Abbreviations and Definitions

Dip G=diptoindonesin G
DMF=dimethylformamide.
ERα=estrogen receptor α; ERβ=estrogen receptor β.
NBS=N-bromosuccinimide (IUPAC name: 1-bromo-2,5-pyrrolidinedione).

A protecting group is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Protective Groups in Organic Synthesis," Theodora W. Greene (John Wiley & Sons, Inc., New York, 1991, ISBN 0-471-62301-6) ("Greene", which is incorporated herein by reference). See also the 5$^{th}$ edition of this same work, published under the title "Greene's Protective Groups in Organic Synthesis," ISBN-13: 978-1118057483, ©2014, John Wiley & Sons, Inc. Greene describes a host of protecting groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups.

A "pharmaceutically suitable salt" is any acid or base addition salt whose counter-ions are non-toxic to a patient (including a veterinary patient) in pharmaceutical doses of the salts, so that the beneficial pharmacological effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage. For example, "one or more" substituents on a phenyl ring designates one to five substituents.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 1A indicates the relative amount of ERα after treating with compounds shown in FIG. 1C. FIG. 1B indicates the relative amount of β-Actin after treating with compounds shown in FIG. 1C.

FIG. 2A indicates the relative amount of FLAG-ERβ after treating with compounds shown in FIG. 2C. FIG. 2B indicates the relative amount of β-Actin after treating with compounds shown in FIG. 2C.

DETAILED DESCRIPTION

Figure 1A:
FIGS. 1A, 1B, and 1C together depict the biological activity of the subject compounds on estrogen receptor α (ERα) levels in human breast cancer cells.
Figure 1B:
Figure 1C:
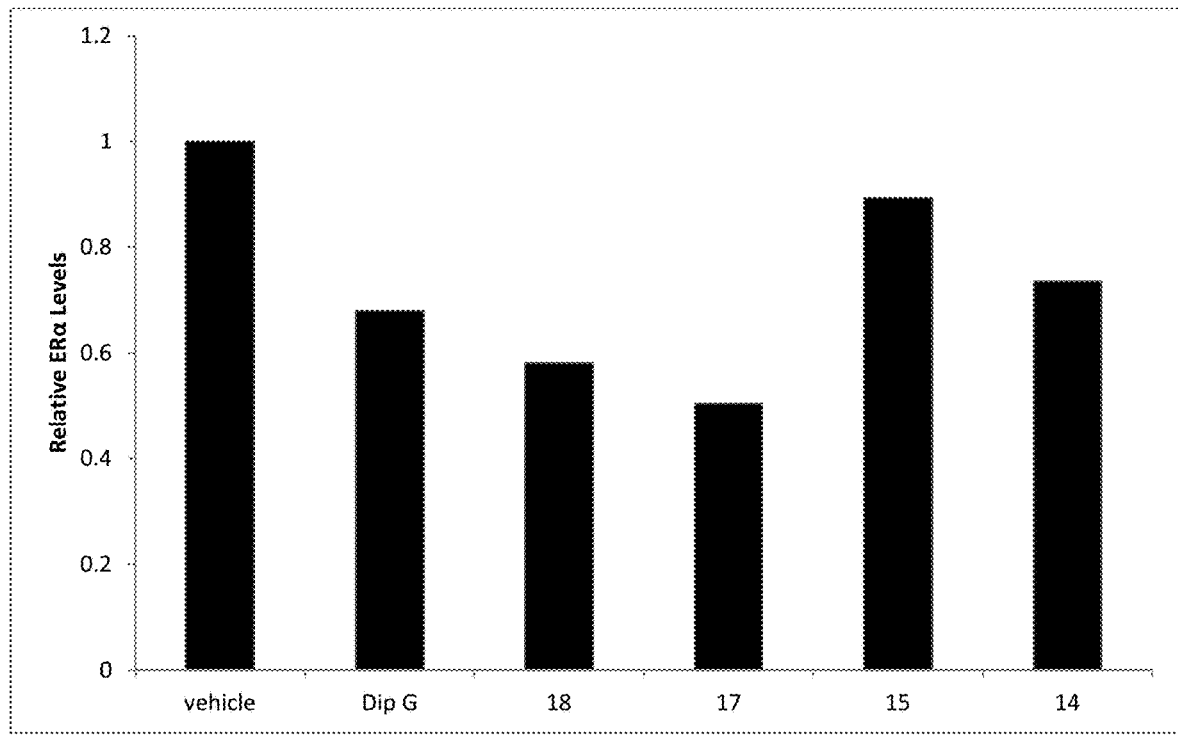
Figure 2A:
FIGS. 2A, 2B, and 2C together depict the biological activity of the subject compounds on estrogen receptor β (ERβ) levels in human breast cancer cells.
Figure 2B:
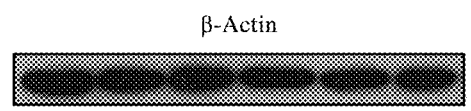
Figure 2C:
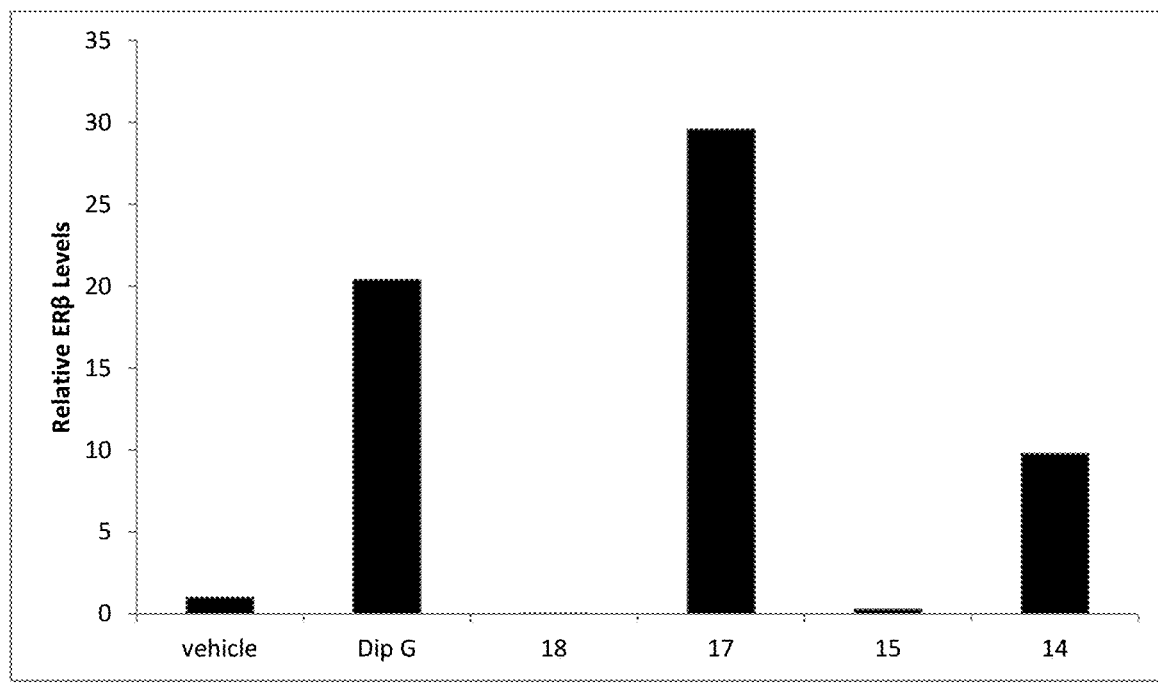

Disclosed herein are novel, unnatural analogues of Dip G. These compounds are active for ameliorating, attenuating, and/or halting the growth and/or metastasis of breast cancers. The compounds have been shown to shrink breast cancer tumors in a murine model of human breast cancer.

The key features of the prior art Kim and Kim synthesis of Dip G include an elegant domino cyclization to construct both B and C rings from a diaryl ether and a Pd-catalyzed C—H arylation to install the E-ring in the penultimate step. For further biological studies of Dip G and its unnatural analogs, there remains an unmet need for a practical and flexible synthetic strategy for this class of compounds. Kim's group has reported that the treatment of 2 with excess $BBr_3$ can lead to the formation of Dip G in high yield directly (Scheme 1). (Kim and Kim, supra.) Disclosed herein is a novel synthetic route in which intermediate 2 was derived from dibromobenzofuran 3 by sequential cross-coupling with two aryl boronic acids. A sequence of alkylation, cyclization, and dibromination converts resorcinol derivative 5 to dibromobenzofuran 3 via benzofuran 4.

Scheme 1: Retrosynthetic Analysis of Dip G

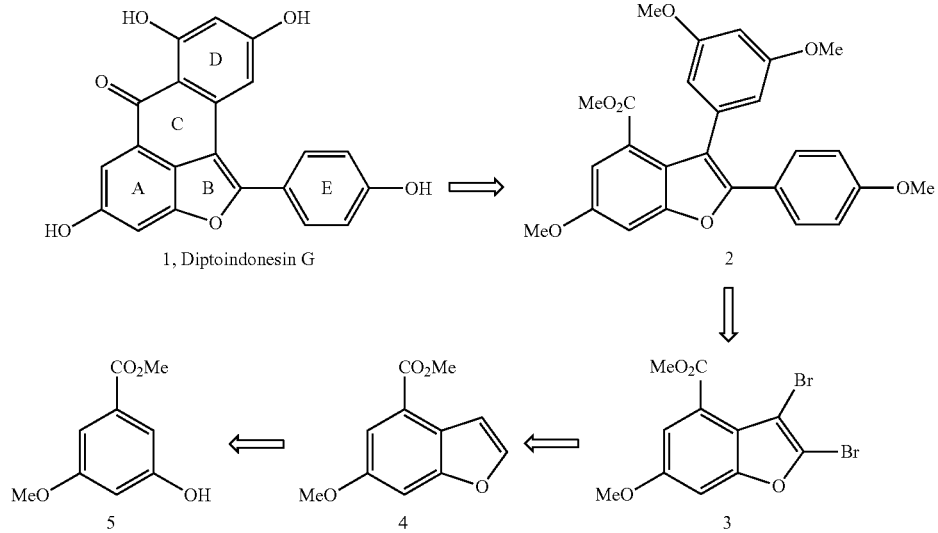

Mono-protected resorcinol derivative 5 is commercially available. It can also be prepared conveniently from methyl 3,5-dihydroxybenzoate. The benzofuran core 4 was synthesized efficiently from 5 by the sequence of alkylation with bromodimethylacetal and cyclodehydration (Scheme 2) using Amberlyst-15. ((a) I. Kim, S.-H. Lee and S. Lee, *Tetrahedron Lett.*, 2008, 49, 6579; b) I. Kim and J. Choi, *Org. Biomol. Chem.*, 2009, 7, 2788; c) J. H. Lee, M. Kim and I. Kim, *J. Org. Chem.*, 2014, 79, 6153.) The cyclization occurred regioselectively, which is consistent with similar reactions reported previously. Id.

Scheme 2: Synthesis of the Benzofuran Core of Dip G

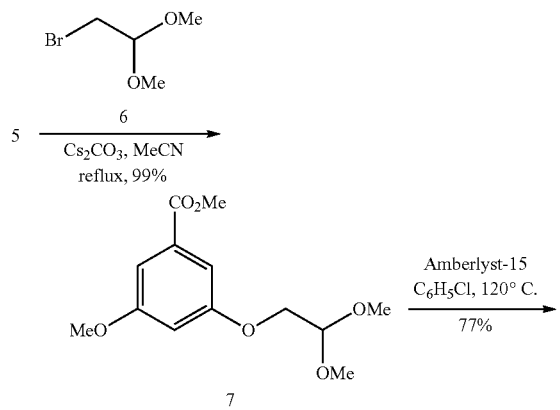

Although there are a number of reports on dibromination of unsubstituted benzofurans (see (a) M. Hussain, N. T. Hung and P. Langer, *Tetrahedron Lett.*, 2009, 50, 3929; (b) J. Chauhan, A. R. Monteil and S. E. Patterson, *Heterocycl. Commun.*, 2010, 16, 241; (c) G. A. Salman, R. U. Nisa, V. O. Iaroshenko, J. Iqbal, K. Ayub and P. Langer, *Org. Biomol. Chem.*, 2012, 10, 9464), it proved impossible to prepare 3 from 4 directly in reliable yields after screening various bromination reagents, solvents, bases, and temperature. See Scheme 3. The carboxylate ester substituent on the 4-position appeared to interfere with the second bromination. The cross-coupling occurred selectively on the 2-position of benzofuran 3. However, the yield of product 8 was low.

Although the sequential Pd-catalyzed cross-coupling reaction for dibromobenzofuran 3 was accomplished via literature methods ((a) N. T. Hung, M. Hussain, I. Malik, A. Villinger and P. Langer, *Tetrahedron Lett.*, 2010, 51, 2420; (b) M. Hussain, N. T. Hung, N. Abbas, R. A. Khera, I. Malik, T. Patonay, N. Kelzhanova, Z. A. Abilov, A. Villinger and P. Langer, *J. Heterocycl. Chem.*, 2015, 52, 497), the yield was not good for the first step.

During the course of optimizing the dibromination of benzofuran 4, it was found that mono-bromination occurred quickly. The second bromination was very slow, and decomposition of brominated products started to occur at high temperature. 2-Bromobenzofuran 9 was isolated in high yield as the only isomer when dichloroethane was used as the solvent and DMF as the catalyst. The direct bromination of benzofurans generally occurred on the more reactive 3-position. ((a) C. J. Hamilton, A. Saravanamuthu, A. H. Fairlamb and I. M. Eggleston, *Bioorg. Med. Chem.*, 2003, 11, 3683; (b) M. Saitoh, J. Kunitomo, E. Kimura, H. Iwashita, Y. Uno, T. Onishi, N. Uchiyama, T. Kawamoto, T. Tanaka, C. D. Mol, D. R. Dougan, G. P. Textor, G. P. Snell, M. Takizawa, F. Itoh and M. Kori, *J. Med. Chem.*, 2009, 52, 6270.) 2-Bromobenzofurans were prepared by lithiation and quenching with electrophilic bromination reagents. ((a) P. Sista, P. Huang, S. S. Gunathilake, M. P. Bhatt, R. S. Kularatne, M. C. Stefan and M. C. Biewer, *J. Polym. Sci., Part A: Polym. Chem.*, 2012, 50, 4316; (b) L. Lu, H. Yan, P. Sun, Y. Zhu, H. Yang, D. Liu, G. Rong and J. Mao, *Eur. J. Org. Chem.*, 2013, 2013, 1644.) The present inventors hypothesized that the carboxylate ester substituent on the 4-position deactivated the 3-position for bromination and this led to the formation of 2-bromobenzofuran only. Pd-catalyzed cross-coupling of 2-bromobenzofuran 9 with 4-methoxyphenyl boronic acid occurred smoothly to afford product 10. 3-Bromobenzofuran 8 was obtained in high yield from 10 after stopping the reaction around 10 min. Longer reaction times led to lower yield of product 8. The second cross-coupling with 3,5-dimethoxyphenyl boronic acid occurred at higher temperature to yield penultimate intermediate 2. Natural product Dip G 1 was prepared from 2 by BBr$_3$-mediated tandem cyclization and demethylation following literature procedure. See Kim and Kim, supra. Up to 0.4 g of Dip G precursor 2 was prepared using this synthetic route.

Scheme 3. Synthesis of Dip G 1 by Sequential Bromination of Benzofurans and Pd-Catalyzed Cross-Couplings

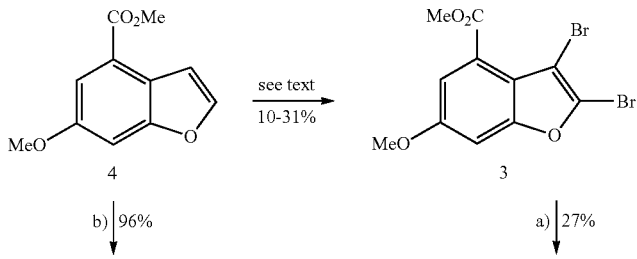

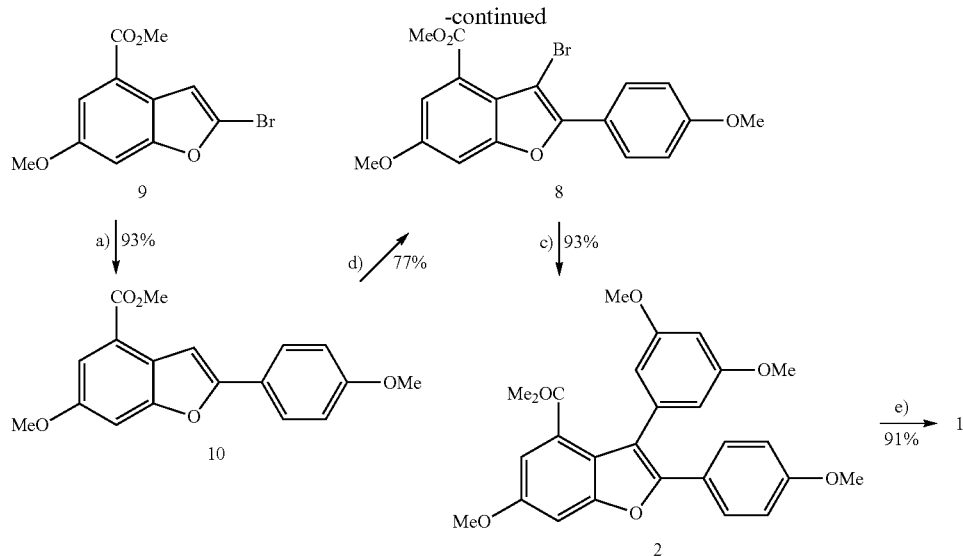

a) Pd(PPh₃)₄ (2.5 mol %), K₂CO₃, 4-MeOC₆H₄B(OH)₂, DMF, 70° C.;
b) NBS, DMF (2 drops), ClCH₂CH₂Cl, 75° C., 3 h;
c) Pd(PPh₃)₄ (5 mol %), K₂CO₃, 3,5-(MeO)₂C₆H₃B(OH)₂, DMF, 110° C.;
d) NBS, ClCH₂CH₂Cl, 70° C., 10 min;
e) excess BBr₃, CH₂Cl₂, -78° C.

To examine the effect of the four phenolic OH groups on biological activity, Dip G analogs were prepared with just two or three phenolic OH groups as shown in Scheme 4. Replacing the para-methoxyphenyl boronic acid by phenyl boronic acid, analog 14 lacking the phenolic OH group in the E-ring of Dip G was prepared from bromobenzofuran 9 in four steps according to the sequence outlined in Scheme 3 for the preparation of 1 from 9. The bromination of 2-phenyl substituted benzofuran 11 proved to be more difficult than the bromination of substrates 4 or 10. Only trace amount of 3-bromobenzofuran 12 was obtained under the conditions shown in Scheme 3 for substrates 4 or 10. The yield could be improved to 50% by using DMF as the co-solvent. Analog 15, which lacks both phenolic OH groups in the D-ring, was Scheme 4: Synthesis of Dip G Analogs

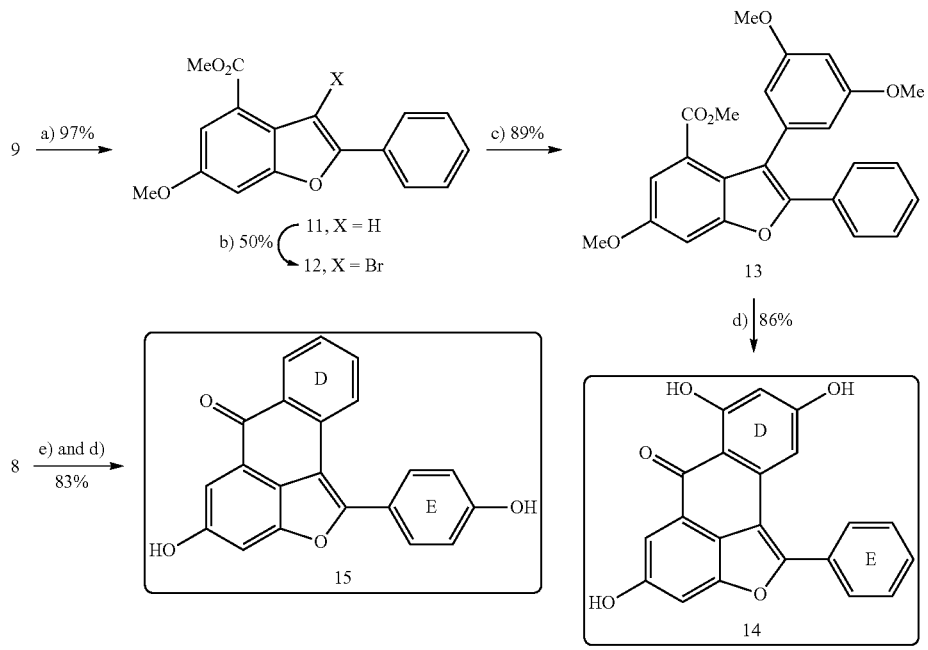

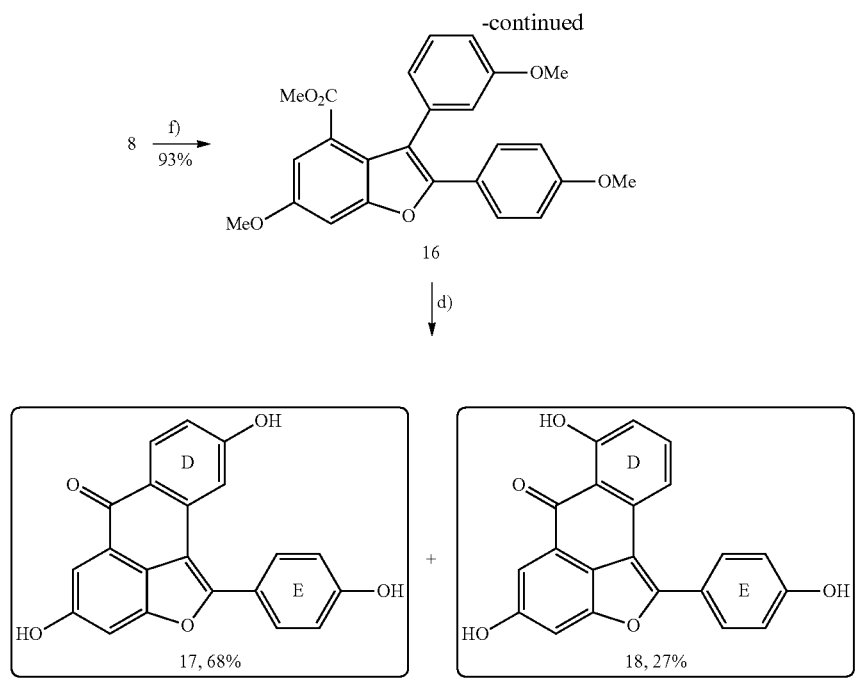

a) Pd(PPh₃)₄ (5 mol %), K₂CO₃, PhB(OH)₂, DMF, 75° C.;
b) NBS, ClCH₂CH₂Cl/DMF (5:1), 80° C.;
c) Pd(PPh₃)₄ (5 mol %), K₂CO₃, 3,5-(MeO)₂C₆H₃B(OH)₂, DMF, 110° C.;
d) excess BBr₃, CH₂Cl₂, -78° C.;
e) Pd(PPh₃)₄ (5 mol %), K₂CO₃, PhB(OH)₂, DMF, 110° C.;
f) Pd(PPh₃)₄ (5 mol %), K₂CO₃, 3-MeOC₆H₄B(OH)₂, DMF, 100° C.

synthesized from intermediate 8 in just two steps. Friedel-Crafts cyclization worked smoothly for the formation of 15 after replacing the electron-rich dimethoxyphenyl group in Dip G 1 by a phenyl group in 15. Finally, compound 16, with just one methoxy group in the D-ring, was prepared from intermediate 8. Products 17 and 18 were formed and the acylation occurred preferentially on the less-hindered position of the D-ring.

The biological activity of these four analogs were then compared with the parent compound Dip G following our previous protocol (Zhao et al., supra). See FIGS. 1A, 1B, 1C, 2A, 2B, and 2C. Cells were treated with each compound at 10 μM concentration in order to evaluate how well each modified the stability of ERα and ERβ. In MCF7 cells, Dip G and all four analogs showed decreased ERα stability with the largest change occurring with Dip G and analogs 17 and 18. In Hs578T-ERβLuc Dox-inducible lines, ERβ was strongly stabilized by Dip G and compound 17. ERβ was moderately stabilized by compound 14. Interestingly, compounds 15 and 18 both destabilized ERβ, suggesting that the hydroxyl group para to the ketone in the D-ring of Dip G was critical for stabilizing ERβ. The hydroxyl group ortho to the ketone in the D-ring of Dip G is dispensable as the activity of compound 17 was slightly better than Dip G for destabilizing ERα and stabilizing ERβ3.

The compounds disclosed herein can also be fabricated via an alternative route, illustrated in Scheme 5:

Scheme 5: Alternative Synthesis of Dip G and Dip G Analogs

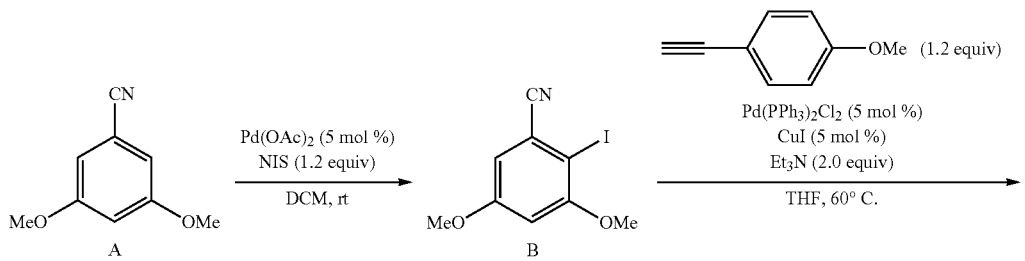

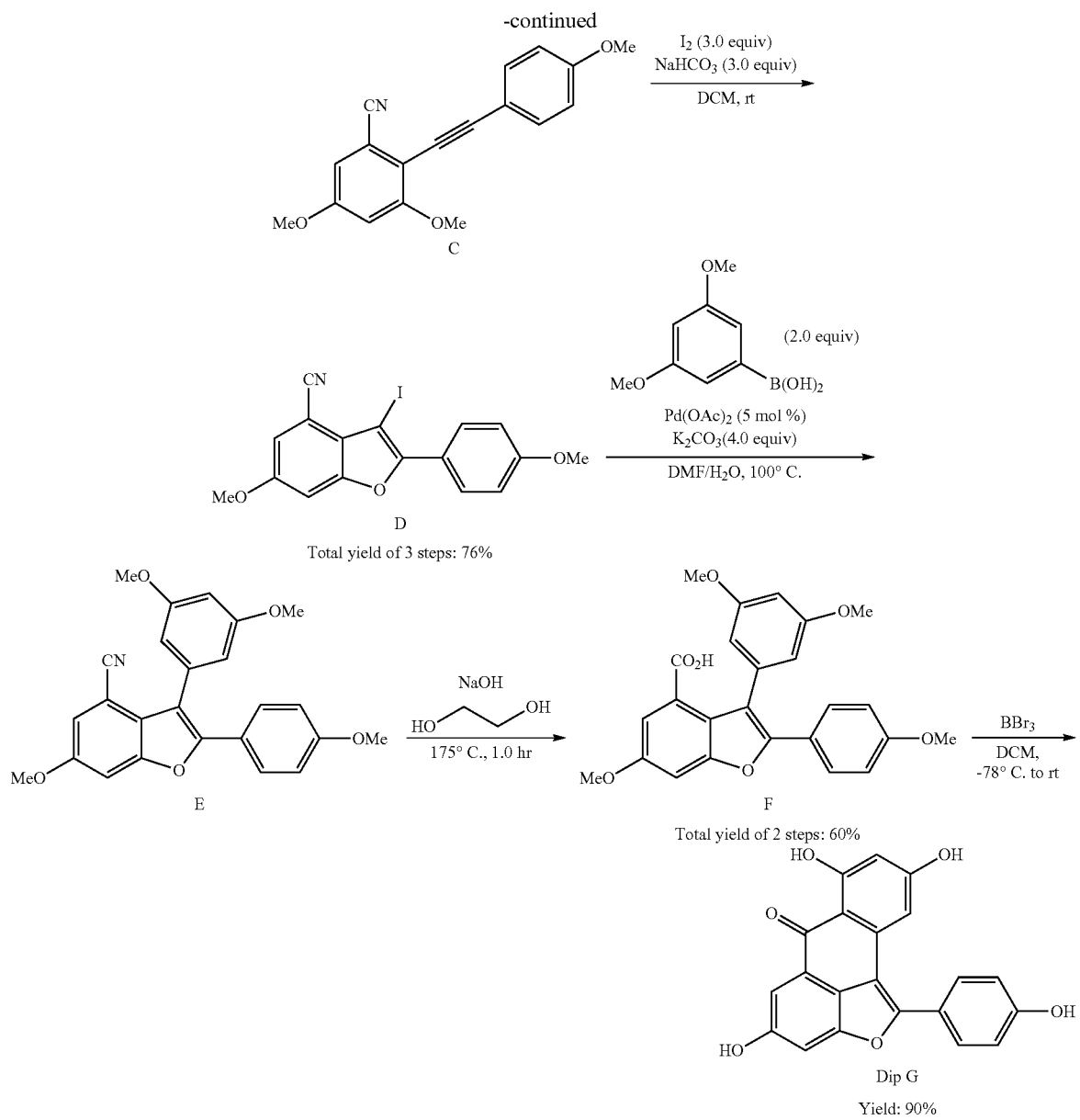

To a stirred solution of nitrile A (61.3 mmol, 10.0 g) in CH$_2$Cl$_2$ (300 mL) were added Pd(OAc)$_2$ (3.1 mmol, 688 mg) and NIS (73.6 mmol, 16.6 g). After being stirred at room temperature for 24 hours, the reaction mixture was quenched by NaHSO$_3$ solution. Then the organic phase was wash by NaHCO$_3$ solution (300 mL) twice. After drying by Na$_2$SO$_4$, the CH$_2$Cl$_2$ solution was concentrated to give a white solid B. The solid was directly used in the next step without further purification.

An oven-dried flask which was charged with Pd(Ph$_3$P)$_2$Cl$_2$ (3.1 mmol, 2.2 g), CuI (3.1 mmol, 584 mg), 4-ethynylanisole (73.6 mmol, 9.7 g) and the materials from last step reaction was evacuated and flushed with argon at rt. The anhydrous THF (300 mL), triethylamine (17 mL) and were sequentially added via syringe. The reaction was protected by argon and stirred at 60° C. overnight. Then the THF was removed and residue was dissolved by CH$_2$Cl$_2$ and washed consecutively with 2.0N HCl solution and brine, dried by Na$_2$SO$_4$ and concentrated under reduced pressure to give light brown solid C, which was directly used in the next step without further purification.

The 1.0 L oven-dried flask was charged with light brown solid from last step, 12 (184 mmol, 46.7 g) and NaHCO$_3$ (184 mmol, 15.5 g) and CH$_2$Cl$_2$ (250 mL). After being stirred at room temperature for 24 hours, 300 mL of water was added to the reaction mixture, NaHSO$_3$ (20.0 g) was added slowly to quench the reaction. After removing the CH$_2$Cl$_2$, 300 mL of ethyl acetate was added to the mixture. The slurry was stirred overnight and filtrated, the filter cake was wash three time by ethyl acetate (30 mL). After drying by high vacuum, 19.0 gram of solid D was obtained. $^1$H NMR (400 MHz, CDCl$_3$) δ 8.07 (d, J=9.0 Hz, 2H), 7.27 (d, J=2.3 Hz, 1H), 7.21 (d, J=2.3 Hz, 1H), 7.02 (d, J=8.9 Hz, 2H), 3.90 (s, 3H), 3.89 (s, 3H).

To a 250-mL flask was added compound D from last step (7.4 mmol, 3.0 g), Pd(OAc)$_2$ (0.37 mmol, 83 mg), (3,5- dimethoxyphenyl) boronic acid (14.8 mmol, 2.7 g) and K$_2$CO$_3$ (29.6 mmol, 4.1 g). After mixture degassing three times and protecting by argon, DMF (74 mL) and H$_2$O (3.7 mL) was added. Then the mixture was heated at 100° C. overnight. After removing DMF, the residue was dissolved in CH$_2$Cl$_2$, and washed by NaHCO$_3$ solution twice, dried by Na$_2$SO$_4$, and concentrated. The light brown solid was directly used in the next step reaction without further purification.

To a 500-mL flask was added compound E from last step, NaOH (35 g) and ethylene glycol (350 mL). Then the mixture was heated at 175° C. for one hour. After cooling to room temperature, the reaction mixture was diluted by 2N HCl (1.0 L), and extracted by CH$_2$Cl$_2$, and the organic phase was dried by Na$_2$SO$_4$, and concentrated. The residue was then purified by silica gel column chromatography (CH$_2$Cl$_2$/Acetone), 1.9 gram of light yellow solid F was obtained. $^1$H NMR (400 MHz, CDCl$_3$) δ 7.51 (d, J=8.9 Hz, 2H), 7.33 (d, J=2.3 Hz, 1H), 7.26 (d, J=2.0 Hz, 1H), 6.82 (d, J=9.0 Hz, 2H), 6.51 (d, J=2.3 Hz, 2H), 6.45 (t, J=2.3 Hz, 1H), 3.93 (s, 3H), 3.80 (s, 3H), 3.72 (s, 6H).

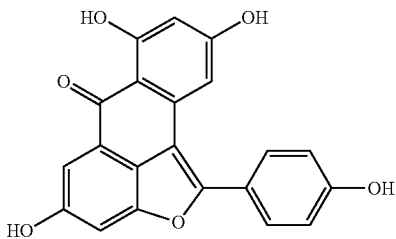

Compound E from the last step (100 mg, 0.23 mmol) was dissolved in CH$_2$Cl$_2$ (28 mL) and treated with BBr$_3$ (CH$_2$Cl$_2$ 1.0M) (6.9 mL, 6.9 mmol) at −78° C. After being stirred at room temperature for 24 h, the reaction mixture was quenched by ice water. The slurry was filtered, washed with water and CH$_2$Cl$_2$, and dried by high vacuum to give Diptoindonesin G (Dip G) 75 mg. $^1$H NMR (400 MHz, Acetone-d6) δ 14.17 (s, 1H), 9.58 (s, 1H), 9.19 (s, 1H), 9.13 (s, 1H), 7.83 (d, J=8.6 Hz, 2H), 7.53 (d, J=1.7 Hz, 1H), 7.34 (d, J=1.8 Hz, 1H), 7.25 (d, J=2.3 Hz, 1H), 7.11 (d, J=8.6 Hz, 2H), 6.37 (d, J=2.2 Hz, 1H).

In summary, disclosed herein is a practical synthetic strategy for the preparation of Dip G and its analogs. The biological evaluation of these new analogs revealed that not all four phenolic hydroxyl groups are required for anti-neoplastic activity.

Activity Against Endocrine-Resistant Breast Cancers:

The subject compounds are effective to inhibit the growth of endocrine-resistant breast cancers, as exemplified by MCF7 cells. Briefly, estrogen receptor ERα is expressed in over 70% of human breast cancers and is a major therapeutic target for endocrine therapy. Although many patients respond to the treatment, approximately 50% of responsive tumors relapse due to the development of resistance. An emerging mechanism of resistance is the development of "hot-spot" mutations in the ligand-binding domain of ESR1, the gene encoding ERα. The mutations lead to ligand-independent ERα activity that promotes tumor growth and metastasis, and reduced binding of ERα antagonists such as tamoxifen and selective estrogen receptor degrader (SERD) such as fulvestrant. Thus the current endocrine treatments are ineffective. As demonstrated herein, Dip G and its analogs significantly decrease ERα protein levels and is insensitive to ESR1 mutations. The compounds disclosed herein are thus effective to inhibit the growth of hormone-resistant breast cancers, including cancers with ESR1 mutations.

Although many patients benefit from Tam and AIs in adjuvant and metastatic settings, approximately 50% of responsive tumors eventually relapse due to the development of resistance. One emerging mechanism of resistance is the clonal evolution of mutations in a "hotspot" within the ligand-binding domain (LBD) of ESR1, the gene encoding ERα. ESR1 mutations occur in 10-20% of patients with metastatic ERα-positive disease who had received endocrine therapies. The mutations lead to ligand-independent ERα activity that promotes cancer growth and metastasis, as well as reduced efficacy of ERα antagonists. The end result is a resistance to endocrine therapies.

To overcome endocrine resistance, one proposed method is to use selective estrogen receptor degraders (SERDs). However, the one currently clinically available, SERD, "FASLODEX"®-brand fulvestrant (AstraZeneca, Cambridge, England), and others in development, only partially degrade ERα. Mutant ERα proteins are even more resistant to fulvestrant-induced degradation. Thus, there is a pressing need to identify a new class of ERα targeting drugs for the treatment of metastatic, ERα-expressing breast cancer.

Figure 4:
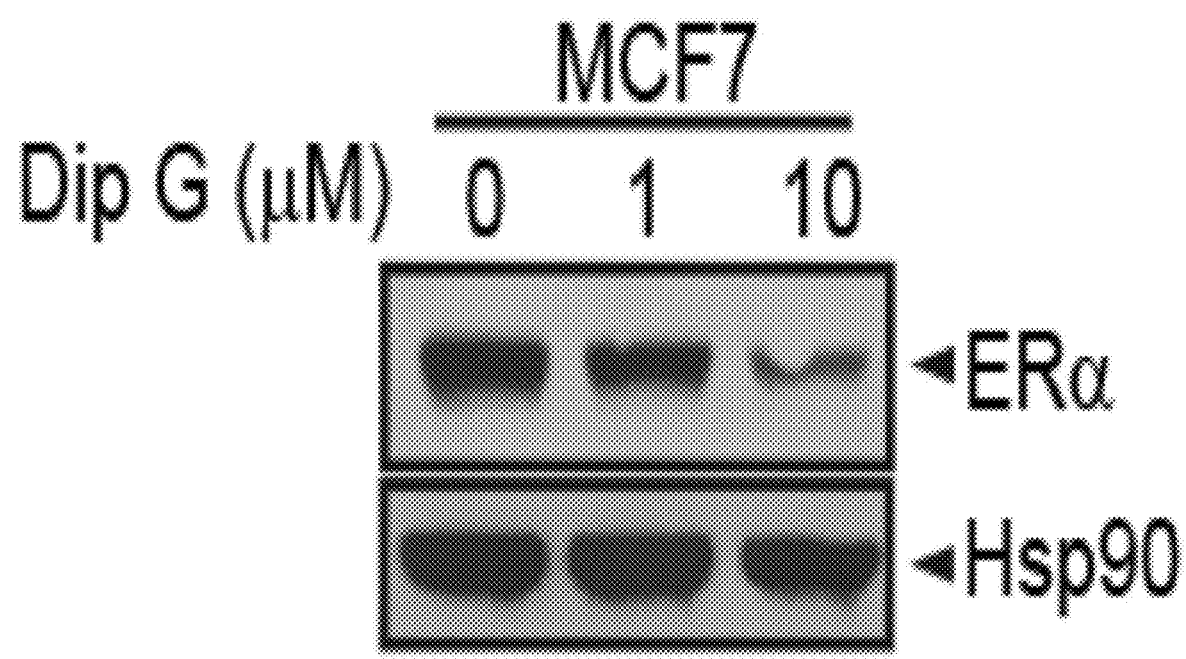
FIG. 4 is a gel blot demonstrating that Dip G degrades endogenous ERα in MCF7 cells.

Dip G promotes mutant ERα protein degradation more effectively than fulvestrant. As shown in FIG. 4, Dip G decreases endogenous ERα protein levels to less than 20% of. It also decreases ERα transcriptional activity in MCF7 cells. See FIG. 4. As shown in FIG. 4, when administered at a concentration of 10 μM, the amount of endogenous ERα in MCF7 cells is greatly decreased as compared to untreated cells. Importantly, using and T47D ERα Y537S stable cell lines, fulvestrant, Dip G and Dip G-D1 degraded wild type ERα proteins with similar efficacy. See FIG. 5. (T47D ERα WT is available from the American Type Culture Collection, Manassas, Va.; accession no. HTB-133. The T47D ERα Y537S cell line is described in Wardell et al 2015) "Efficacy of SERD/SERM Hybrid-CDK4/6 Inhibitor Combinations in Models of Endocrine Therapy-Resistant Breast Cancer," *Clin Cancer Res.* 21(22):5121-5130. Dip G and Dip G-D1 are more effective than 100 nM fulvestrant to degrade ERαY537S mutant protein. See FIG. 5. It is worthy to mention that the peak plasma concentration of fulvestrant in patients following the high dose administration of fulvestrant (500 mg) is ~20 ng/ml (~30 nM). McCormack, P. and Sapunar, F. (2008) "Pharmacokinetic profile of the fulvestrant loading dose regimen in postmenopausal women with hormone receptor-positive advanced breast cancer," *Clinical breast cancer* 8:347-351. Pritchard, K. I., Rolski, J., Papai, Z., Mauriac, L., Cardoso, F., Chang, J., Panasci, L., Ianuli, C., Kahan, Z., Fukase, K. et al. (2010) "Results of a phase II study comparing three dosing regimens of fulvestrant in postmenopausal women with advanced breast cancer (FINDER2)," *Breast cancer research and treatment* 123: 453-461. The 100 nM of fulvestrant used in vitro is much higher the therapeutic dose in vivo. No obvious toxicity was observed in vivo for high concentrations of Dip G. (See below for further discussion.) This finding supports Dip G as a novel ERα degradation agent for mutant ERα in endocrine-resistant tumors.

Dip G inhibited growth of T47D xenograft tumor in vivo. Dip G was synthesized as described and formulated for the in vivo treatment. Dip G was prepared by dissolving the stock powder in 100% DMSO to a final concentration of 50 mg/ml. This stock solution was then diluted 1:5 into a 40% polyethylene glycol (PEG300)/40% normal saline (0.9%

Figure 3:
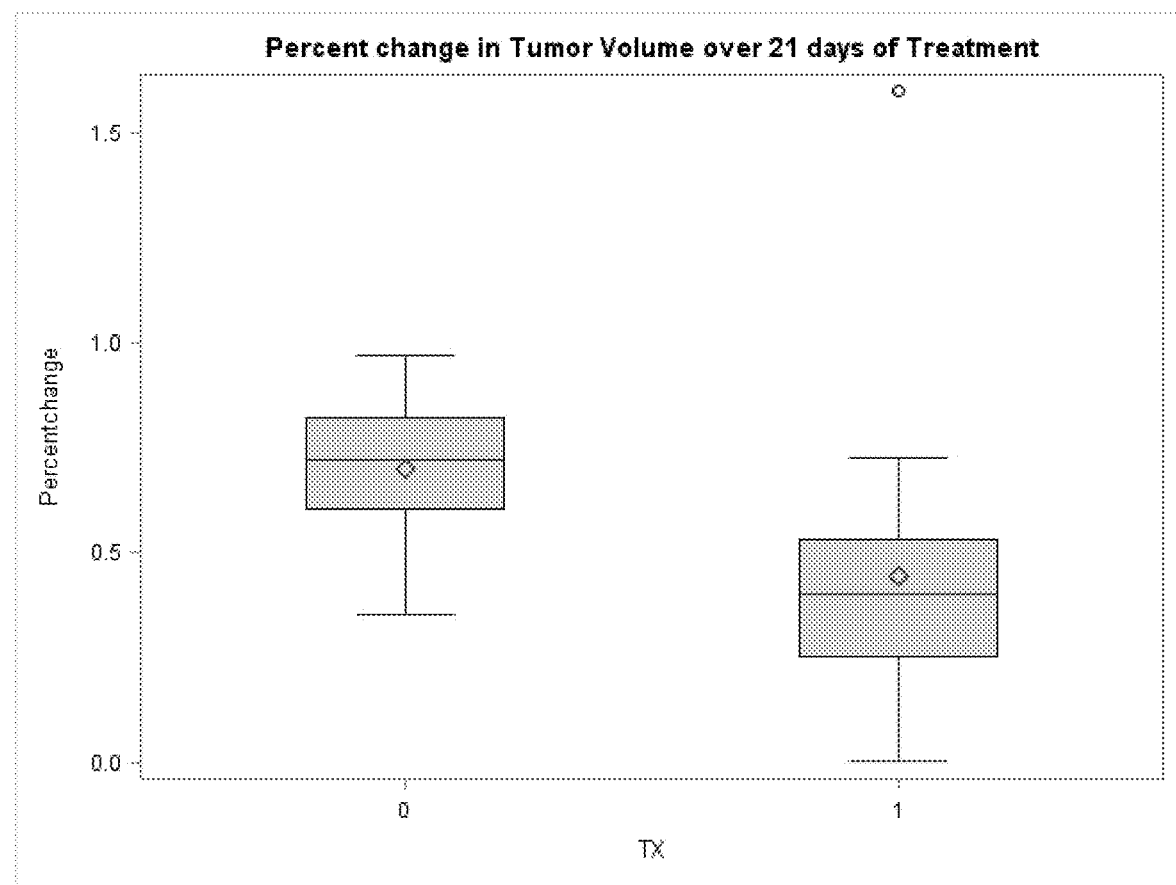
FIG. 3 is a histogram depicting percent decrease in tumor volume over 21 days of treatment with Dip G in a murine model of human breast cancer. See the Examples for complete experimental details. 0=Control, 1=Dip G.

NaCl) solution to a final concentration of 20% Dip G solution. The maximum tolerated dose (MTD) of Dip G was determined to be 50 mg/kg by oral and 20 mg/kg by retro-orbital injection in mouse models. To determine MTD, escalating doses of Dip G dissolved in the aforementioned formulation were injected retro-orbitally or by oral gavage daily, five days out of seven to determine the MTD. To evaluate the pharmacokinetics of Dip G, the 3P Lab at the University of Wisconsin Carbon Cancer Center developed a HPLC and LC/MS method for measuring the plasma concentrations of Dip G. Dip G was found to have half-life of 1 hour in mice. (Data not shown.) Dip G was intra-tumorally delivered to ERα-positive T47D xenografted mice three times a week and the tumors were monitored for three weeks. See FIG. 3. It was found that treatment with Dip G for 21 days strongly inhibited xenografted tumor growth as compared with vehicle-treated controls. Control-treated tumors were 70% of original size, while tumors (n=16) treated with Dip G were 46% of original size (FIG. 3). Under these treatment conditions, some Dip G-treated tumors completely regressed. Liver toxicity was undetectable using an aspartate aminotransferase ("AST"))ELISA assay (AST activity was around 70 milliunits/mL) and no gross tissue damages were observed in liver, lung, kidney, brain, and heart. (AST ELISAs are available commercially from several suppliers, including Abcam, Cambridge, Mass.)

Mechanistically, it was determined that Dip G does not directly bind to ERα; rather it binds to CHIP ubiquitin E3 ligase that regulates the stability of ERα. This finding is important because this indirect mode of action distinguishes Dip G from other known ERα targeting agents that bind to ERα directly. Prior to this study, the in vivo anti-cancer effect of Dip G has never been investigated. Dip G is thus effective in overcoming endocrine resistance regardless of the basis (genetic or otherwise) of that resistance. Dip G and its analogues is therefore likely more effective and less toxic fulvestrant for treating metastatic breast cancers.

Additional experiments are currently being conducted to determine the toxico-kinetics and pre-clinical pharmacology of Dip G and Dip G-D1 (compound 17) in mice. We will examine if HPLC and LC/MS methods developed for measuring plasma concentrations of Dip G also measures Dip G-D1. Escalating doses of Dip G-D1 dissolved in PBS will be injected retro-orbitally daily, five days out of seven to determine the MTD. The body weight, as well as acute toxicities of the mice (female and male, n=3 each) will be monitored for up to one month to determine MTD of Dip GD1.

The MTD determined above will be administered IV retro-orbitally into mice. Blood will be withdrawn and the concentration of Dip G-D1 will be measured to determine the pharmacokinetics (half-life, area under the curve, Cmax, etc) of the compound in vivo. For toxico-kinetics study, we will administer low, mid, and high doses of Dip G and Dip G-D1 to male and female mice for 14 consecutive days. Clinical pathology observations including hematology, coagulation, clinical chemistry, and urinalysis evaluations will be determined at the time of termination.

Finally, we will measure the concentration of Dip G or its analogue in tumors taken from MCF7 xenografts in athymic nude mice. Our lab has performed MCF7 xenografts previously; see Al-Dhaheri, M., Wu, J., Skliris, G. P., Li, J., Higashimato, K., Wang, Y., White, K. P., Lambert, P., Zhu, Y., Murphy, L. et al. (2011) "CARM1 is an important determinant of ERalpha-dependent breast cancer cell differentiation and proliferation in breast cancer cells," *Cancer research* 71:2118-2128. Briefly, $5\times10^6$ MCF7 cells will be inoculated into the mammary fat pad of nude mice (n=5). 25 mg, 60-day slow releasing 17β-estradiol pellets (Innovative Research of America, Sarasota, Fla.) will be implanted into mice two days afterward. Animals will be monitored for palpable tumor formation. Usually after 4 weeks, MCF7 xenograft tumors reach 100-200 mm$^3$. We will then administer Dip G or its analogue retro-orbitally or by oral gavage into mice and excise the tumors to analyze intratumoral concentration of the compound.

We will also assess the anti-cancer effect of Dip G in MCF7 derivative cell lines and xenograft mouse models. We will first compare the efficacy of Dip G and Dip G analogues to degrade ER, to inhibit transcriptional activity of ERα mutants, and to block cell proliferation in MCF7 cells expressing ERα mutants. We will use three different MCF7 derivative cell lines, each expressing an ERα mutant having a single point mutation Y537S, Y537N and D538G to the comparable level of endogenous wild type ERα. These cell lines are described in the literature and we recently obtained from Dr. Ben Ho Park (John Hopkins U.). See Scott, G. K. et al. (2016) "ERpS294 is a biomarker of ligand or mutational ERα activation and a breast cancer target for CDK2 inhibition," Oncotarget, DOI: 10.18632/oncotarget. 12735.

Figure 5:
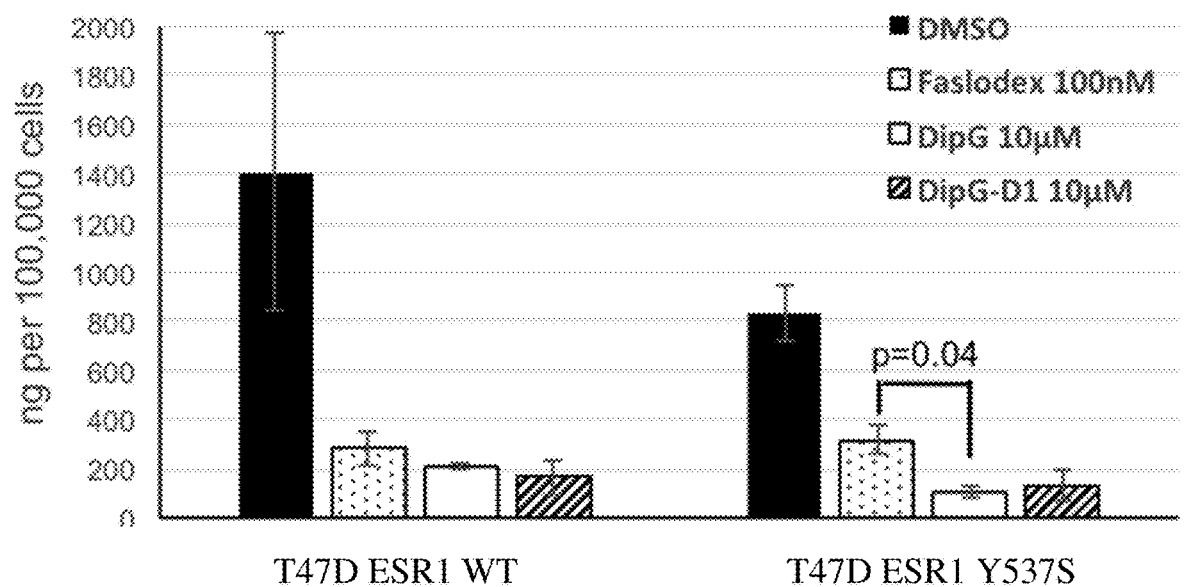
FIG. 5 is a histogram depicting degradation of ERα in T47D-ERαWT and T47D-ERαY537S cells. T47D cells were treated with DMSO, Fulvestrant, Dip G and a Dip G derivative (Dip G-D1, compound 17) for 24 hrs. ERα protein amounts in cell lysate were quantified using ELISA kit (R&D systems) and normalized to standard curve using purified ERα protein. The experiments were performed in triplicate. Data are represented as mean±SD, n=3.
Figure 6:
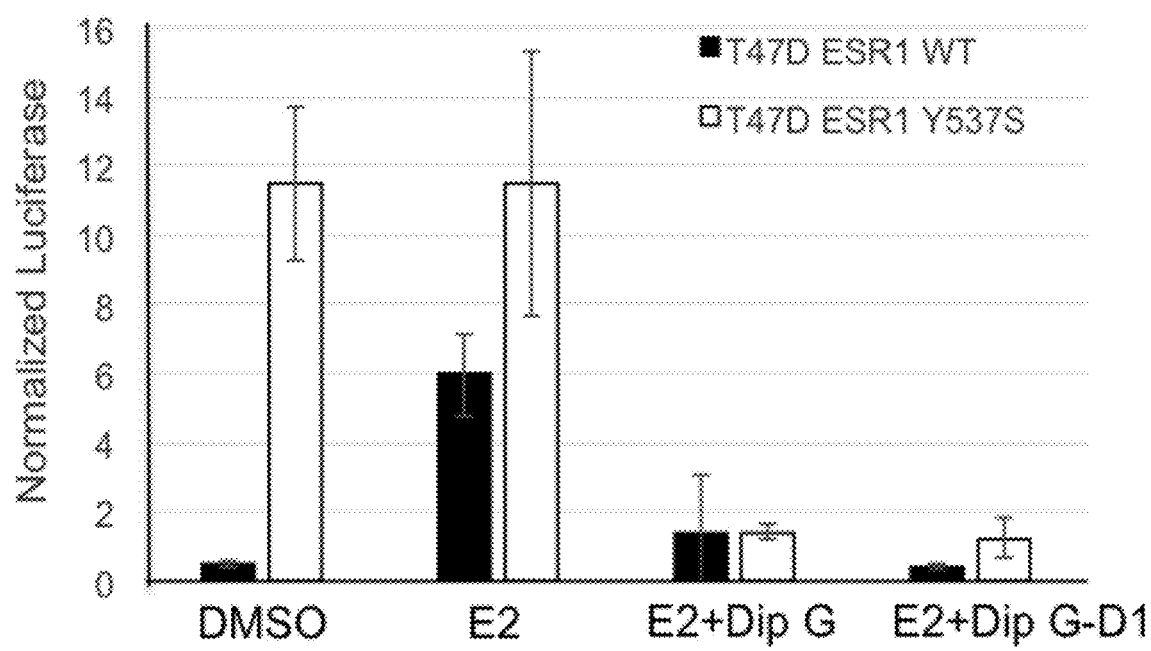
FIG. 6 is a histogram depicting Dip G- and Dip G-D1-inhibited E2-dependent ERE-Luciferase activities of wild-type ERα or ERα Y537S in T47D cells. Cells were co-treated with 10 nM E2 and Dip G or Dip G-D1 (10 μM) for 24 hrs. The experiments were performed in triplicate. Data are represented as mean±SD, n=3.

Previous studies have shown that the exogenously expressed mutant ERα displayed a significantly reduced response to Tam and fulvestrant, and approximately 30-100-fold higher doses of anti-estrogens are needed to achieve the level of inhibition in these cell lines as compared with the dose required in cells expressing the wild type ERα. See Merenbakh-Lamin, K., Ben-Baruch, N., Yeheskel, A., Dvir, A., Soussan-Gutman, L., Jeselsohn, R., Yelensky, R., Brown, M., Miller, V. A., Sarid, D. et al. (2013) "D538G mutation in estrogen receptor-alpha: A novel mechanism for acquired endocrine resistance in breast cancer," *Cancer research*, 73:6856-6864 and Jeselsohn, R., Yelensky, R., Buchwalter, G., Frampton, G., Meric-Bernstam, F., Gonzalez-Angulo, A. M., Ferrer-Lozano, J., Perez-Fidalgo, J. A., Cristofanilli, M., Gomez, H. et al. (2014) "Emergence of constitutively active estrogen receptor-alpha mutations in pretreated advanced estrogen receptor-positive breast cancer," *Clinical cancer research: an official journal of the American Association for Cancer Research*, 20:1757-1767. Using these ERα mutant expressing cell lines, we will: (a) compare ERα degradation rate induced by fulvestrant, Dip G and Dip G-D1 using ELISA assay as shown in FIG. 5; (b) measure IC50 of Dip G and Dip G analogues to inhibit ERα transcriptional activity in luciferase assay. Our preliminary data showed that ERα-positive cell line T47D expressing ERα Y537S mutant elicits ligand-independent transcription activity (see FIG. 7) which can be inhibited by Dip G and DipG-D1; and (c) compare the effects of Dip G or its analogues, Tam and fulvestrant on the growth of MCF7 ER WT, Y537S, Y537N and D538G cells in the absence and presence of 10 nM E2.

We expect that Dip G and its analogues promote ERα degradation and inhibit cell proliferation even in cells expressing mutant ERα.

We will also assess in vivo effects of Dip G and a Dip G analogue in MCF7-derivative cell line xenografts. We will use Tam-resistant MCF7-derivative cell lines MCF7/LCC2, an anti-estrogen resistant model not caused by ERα mutation (see Brunner et al. (1993) "MCF7/LCC2: a 4-hydroxytamoxifen resistant human breast cancer variant that retains sensitivity to the steroidal anti-estrogen ICI 182, 780," *Cancer research* 53:3229-3232) and MCF7 ERα Y537S, Tam resistant model caused by ERα mutation for xenografts, followed by treatment with vehicle or Dip G and Dip G analogues that exhibit the strongest in vitro activity.

LCC2 or MCF7 ERY537S cells ($2\times10^6$) will be orthotopically implanted into ovariectomized, athymic nude mice (5-week old, n=10) with or without E2 supplementation, as described in Wang, L., Zhao, Z., Meyer, M. B., Saha, S., Yu, M., Guo, A., Wisinski, K. B., Huang, W., Cai, W., Pike, J. W. et al. (2014) "CARM1 methylates chromatin remodeling factor BAF155 to enhance tumor progression and metastasis," *Cancer Cell* 25:21-36. Mean tumor size will be measured weekly until the tumors reach 100 mm³. There will be a total of 4 groups (LCC2-E2, LCC2+E2, MCF7 ERY537S-E2, MCF7 ERY537S+E2). Each group (n=40) will be treated with phosphate-buffered saline (PBS), fulvestrant, Dip G, a Dip G analogue at 40 mg/kg by oral gavage for 21 consecutive days. 200 mg/kg of fulvestrant will be given by subcutaneous injection weekly. Tumor volume will be measured every other day. If tumor size reaches 500 mm³ or decreases to ⅓ of the original size, BrdU will be injected into mice one-hour prior to sacrifice. Tumors will be collected for IHC staining of ERα, BrdU and Ki67. The concentration of Dip G or its analogue in plasma and tumors will be determined using HPLC/MS/MS. ERα protein levels in tumors will be quantified using ELISA assay. We anticipate that the LCC2 cells will grow to tumors regardless of E2 but its growth will be stimulated by estrogen supplementation. We expect that Dip G and Dip G analogue treatment will lead to tumor regression, ERα degradation, and decrease of the proliferation index BrdU staining and Ki67.

Pharmaceutical Compositions:

Also disclosed herein are pharmaceutical compositions comprising one or more of the DIP G analogs or a pharmaceutically suitable salt thereof as described herein. More specifically, the pharmaceutical composition may comprise one or more of the DIP G analogs as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, DIP G analogs produced as described herein can be tableted with conventional tablet bases such as lactose, sucrose, and corn starch in combination with binders such as acacia, corn starch or gelatin, disintegrating agents such as potato starch or alginic acid, and a lubricant such as stearic acid or magnesium stearate. Capsules can be prepared by incorporating these excipients into a gelatin capsule along with antioxidants and the relevant DIP G analog.

For intravenous and intra-tumor administration, the DIP G analogs may be incorporated into commercial formulations such as Intralipid©-brand fat emulsions or other suitable vehicles well-known in the pharmaceutical arts. ("Intralipid" is a registered trademark of Fresenius Kabi A B, Uppsalla, Sweden.) Where desired, the individual components of the formulations may be provided individually, in kit form, for single or multiple use. A typical intravenous dosage of a representative DIP G analog as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the art and depends upon various factors such as weight of the patient, age of the patient, medical condition of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating neoplastic disorders in mammals, including humans, by administering an anti-neoplastic-effective amount of one or more the DIP G analogs described herein. In particular, the compositions of the present invention may be used to treat neoplastic conditions of any and all description, including bladder cancer, lung cancer, brain cancer, melanoma, breast cancer, non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, uterine cancer, and the like.

The above-described pharmaceutical compositions can be utilized in non-human animals, both domestic and non-domestic, as well as in humans.

EXAMPLES

The following examples are includes solely to provide a more complete description of the invention disclosed and claimed herein. The examples do not limit the scope of the claims in any fashion.

General Remarks:

All reactions in non-aqueous media were conducted under a positive pressure of dry argon in glassware that had been oven dried prior to use unless noted otherwise. Oxygen and moisture-sensitive reactions were carried out under an argon atmosphere. Solvents were purified and dried by standard methods prior to use. All commercially available reagents were used without further purification unless otherwise noted. Thin layer chromatography was performed using pre-coated silica gel plates (EMD Millipore, Billerica, Mass., silica gel 60 $F_{254}$ coated glass-backed TLC plates).

Flash column chromatography was performed with silica gel (Sillicycle, Quebec City, Canada; 40-63 m). Infrared spectra (IR) were obtained as neat oils on a Bruker Equinox 55 Spectrophotometer (Bruker AXS Inc., Fitchburg, Wis.). $^1$H and $^{13}$C Nuclear magnetic resonance spectra (NMR) were obtained on a Varian Unity-Inova 400 MHz or 500 MHz recorded in ppm (δ) downfield of TMS (δ=0) in CDCl$_3$ or (CD$_3$)$_2$CO or (CD$_3$)$_2$SO (Varian, Inc. formerly a wholly owned subsidiary of Agilent Technologies; closed operations in October 2014.). Signal splitting patterns were described as singlet (s), doublet (d), triplet (t), quartet (q), quintet (quint), or multiplet (m), with coupling constants (J) in Hertz. High resolution mass spectra (HRMS) were performed by the Analytical Instrument Center at the School of Pharmacy or Department of Chemistry of University of Wisconsin—Madison, on an electron spray injection (ESI) mass spectrometer.

Procedure for Western Blot Analyses:

MCF7 cells were treated with Dip G and analogs for 24 hours before harvesting. Hs578T-tet-on-ERβ cells (ATCC HTB-126; American Type Culture Collection, Manassas, Va.) were treated with doxycycline for 24 hours to induce ERβ expression. Then the cells were treated with compounds for 5 days before harvesting. 15 μg of total cell lysates were resolved on SDS-PAGE and Western blot analyses were performed as previously described using ERα antibody (HC-20, Santa Cruz Biotechnology, Inc., Dallas, Tex.) and anti-FLAG antibody (F7425, Sigma-Aldrich Co., LLC, St. Louis, Mo.) for ERβ.[3]

Procedure for the Preparation of 7:

To a mixture of phenol 5 (0.9 g, 4.95 mmol) and Cs$_2$CO$_3$ (3.3 g, 10 mmol) in 30 mL of MeCN was added 2-bromo-1,1-dimethoxyethane (0.9 mL, 7.5 mmol) at room temperature. The mixture was stirred at reflux for 40 h before the reaction was completed. After cooling down, water was added and extracted with ethyl acetate three times. The combined organic phase was collected, concentrated, and purified on a flash column to give methoxybenzoate 7 (1.33 g, 4.9 mmol, 99%) as a colorless oil. $^1$H NMR (400 MHz, CDCl$_3$, TMS): δ 3.46 (s, 6H), 3.81 (s, 3H), 3.89 (s, 3H), 4.02 (d, J=5.2 Hz, 2H), 4.72 (t, J=5.2 Hz, 1H), 6.68 (t, J=2.4 Hz, 1H), 7.19 (d, J=2.4 Hz, 2H); $^{13}$C NMR (100 MHz, CDCl$_3$): δ 52.4, 54.3, 55.7, 68.0, 102.1, 106.4, 107.7, 107.9, 132.2, 159.7, 160.8, 166.8; IR: ν 3384, 2365, 1715, 1260, 1179, 736 cm$^{-1}$. HRMS (ESI) for C$_{13}$H$_{18}$NaO$_6$ (M+Na), (Calc.) 293.0995, found 293.0985.

Procedure for the Preparation of 4:

To a solution of methoxybenzoate 7 (1.3 g, 4.8 mmol) in 40 mL of chlorobenzene was added Amberlyst-15 (130 mg, 10 wt %). The mixture was heated at 120° C. for 3 h. After cooling down to room temperature, the mixture was filtered and the volatile solvent was removed under reduced pressure to give a yellow residue. The residue was purified by flash column to give 4 (760 mg, 3.7 mmol, 77%) as a white solid. m.p.=49-50° C. $^1$H NMR (400 MHz, CDCl$_3$, TMS): δ 3.84 (s, 3H), 3.94 (s, 3H), 7.18 (dd, J=0.9, 2.3 Hz, 1H), 7.21 (dd, J=0.9, 2.2 Hz, 1H), 7.55 (d, J=2.3 Hz, 1H), 7.59 (d, J=2.3 Hz, 1H); $^{13}$C NMR (100 MHz, CDCl$_3$): δ 52.2, 56.1, 101.5, 107.7, 113.4, 121.7, 122.8, 145.7, 156.4, 157.4, 166.8; IR: ν 3406, 2340, 1600, 1348, 1196, 770 cm$^{-1}$. HRMS (ESI) for C$_{11}$H$_{10}$NaO$_4$ (M+Na), (Calc.) 229.0471, found 229.0469.

Procedure for the Preparation of 3:

To a solution of carboxylate 4 (100 mg, 0.49 mmol) in 5 mL of DMF was added NBS (360 mg, 1.5 mmol) in one portion. The mixture was heated at 70° C. for 4 h before the reaction was completed. Saturated Na$_2$S$_2$O$_3$ solution was added and extracted with ethyl acetate for three times. The combined organic phase was collected, concentrated and purified by flash column to give 3 (55 mg, 0.15 mmol, 31%) as a white solid. m.p.=92-94° C. $^1$H NMR (400 MHz, CDCl$_3$, TMS): δ 3.87 (s, 3H), 3.98 (s, 3H), 7.11 (d, J=2.4 Hz, 1H), 7.34 (d, J=2.4 Hz, 1H); $^{13}$C NMR (100 MHz, CDCl$_3$): δ 52.4, 56.3, 99.0, 99.9, 114.4, 119.0, 124.8, 130.6, 156.4, 157.7, 166.4; IR: ν 3385, 1720, 1622, 1314, 1127, 734 cm$^{-1}$. HRMS (ESI) for C$_{11}$H$_8$Br$_2$NaO$_4$ (M+Na) 386.8667, (Calc.), found 386.8664.

Procedure for the Preparation of 9:

To a solution of 4 (412 mg, 2 mmol) in 20 mL of 1,2-dichloroethane was added NBS (540 mg, 3 mmol) and 0.1 mL DMF. The mixture was stirred at 70° C. for 3 h before all the substrate was converted to the product. Sat. Na$_2$S$_2$O$_3$ solution was added to quench the reaction and extracted with ethyl acetate. The combined organic phase was collected, concentrated and purified by flash column to give carboxylate 9 (545 mg, 1.91 mmol, 96%) as white solid. m.p.=92-93° C. $^1$H NMR (400 MHz, CDCl$_3$, TMS): δ 3.87 (s, 3H), 3.97 (s, 3H), 7.16 (dd, J=0.9, 2.3 Hz, 1H), 7.20 (d, J=0.9 Hz, 1H), 7.56 (d, J=2.3 Hz, 1H); $^{13}$C NMR (100 MHz, CDCl$_3$): δ 52.4, 56.3, 101.3, 109.5, 113.5, 122.0, 122.9, 128.8, 157.0, 157.3, 166.4; IR: ν 3407, 2360, 1717, 1317, 1143, 736 cm$^{-1}$. HRMS (ESI) for C$_{11}$H$_9$BrNaO$_4$ (M+Na), (Calc.) 306.9576, found 306.9578.

Procedure for the Preparation of 10:

To a 50 mL flask was added 9 (540 mg, 1.9 mmol), (4-methoxyphenyl)boronic acid (590 mg, 3.8 mmol), K$_2$CO$_3$ powder (1.3 mg, 10 mmol) and DMF (30 mL). The mixture was degassed three times for a total time of 30 min before Pd(PPh$_3$)$_4$ (60 mg, 0.05 mmol) was added. The flask was degassed again and refilled with argon. The mixture was heated at 70° C. overnight. Water was added and the mixture extracted with ethyl acetate three times. The organic phase was collected and washed with brine. The organic layer was dried with Na$_2$SO$_4$, concentrated and purified on silica gel to give 10 (5.5 mg, 1.76 mmol, 93%) as a white solid. m.p.=101-103° C. $^1$H NMR (400 MHz, CDCl$_3$, TMS): δ 3.87 (s, 3H), 3.90 (s, 3H), 4.00 (s, 3H), 6.97 (d, J=9.0 Hz, 2H), 7.25 (dd, J=0.9, 2.3 Hz, 1H), 7.39 (d, J=0.9 Hz, 1H), 7.56 (d, J=2.3 Hz, 1H), 7.79 (d, J=9.0 Hz, 2H); $^{13}$C NMR (100 MHz, CDCl$_3$): δ 52.0, 55.3, 56.0, 100.6, 101.4, 112.5, 114.3, 121.7, 123.0, 124.0, 126.4, 156.0, 156.7, 157.0, 160.1, 166.8; IR: ν 3404, 2359, 1715, 1531, 1175, 766 cm$^{-1}$. HRMS (ESI) for C$_{18}$H$_{16}$NaO$_5$ (M+Na), (Calc.) 335.0890, found 335.0875.

Procedure for the Preparation of 8:

To a solution of 10 (550 mg, 1.76 mmol) in 30 mL of 1,2-dichloroethane was added NBS (470 mg, 2.64 mmol). The mixture was stirred at 70° C. for 10 min before the reaction was completed. Saturated Na$_2$S$_2$O$_3$ solution was added to quench the reaction and extracted with ethyl acetate three times. The combined organic phase was collected, concentrated and purified by flash column chromatography to give bromide 8 (510 mg, 1.31 mmol, 77%) as a white solid. m.p.=109-110° C. $^1$H NMR (400 MHz, CDCl$_3$, TMS): δ 3.85 (s, 3H), 3.86 (s, 3H), 3.99 (s, 3H), 6.97 (d, J=9.0 Hz, 2H), 7.12 (d, J=2.3 Hz, 1H), 7.23 (d, J=2.3 Hz, 1H), 8.02 (d, J=9.0 Hz, 2H); $^{13}$C NMR (100 MHz, CDCl$_3$): δ 52.2, 55.4, 56.0, 90.8, 99.3, 113.1, 114.0, 120.0, 122.0, 125.4, 128.9, 152.0, 154.7, 157.4, 160.3, 167.0; IR: ν 3369, 1716, 1503, 1309, 1134, 735 cm$^{-1}$. HRMS (ESI) for C$_{18}$H$_{15}$BrNaO$_5$ (M+Na), (Calc.) 412.9995, found 412.9975.

Procedure for the Preparation of 2:

To a 50 mL flask was added bromide 8 (390 mg, 1 mmol), (3,5-dimethoxyphenyl)boronic acid (570 mg, 3 mmol), K$_2$CO$_3$ power (700 mg, 5 mmol) and DMF (30 mL). The mixture was degassed three times for a total time of 30 min before Pd(PPh$_3$)$_4$ (55 mg, 0.05 mmol) was added. The flask was degassed again and refilled with argon. Then the mixture was heated at 110° C. for 4 h. Water was added and the aqueous solution was extracted with ethyl acetate three times. The organic phases were combined and washed with brine. Then the organic layer was dried with Na$_2$SO$_4$, concentrated and purified by flash column chromatography with 10% acetone in hexane as fluent to give 2 (415 mg, 0.93 mmol, 93%) as a light yellow oil. $^1$H NMR (400 MHz, CDCl$_3$, TMS): δ 3.23 (s, 3H), 3.77 (s, 6H), 3.80 (s, 3H), 3.90 (s, 3H), 6.50 (s, 3H), 6.81 (d, J=9.0 Hz, 2H), 7.21 (d, J=2.3 Hz, 1H), 7.24 (d, J=2.3 Hz, 1H), 7.47 (d, J=9.0 Hz, 2H); $^{13}$C NMR (100 MHz, CDCl$_3$): δ 51.5, 55.3, 55.5, 56.1, 99.6, 100.1, 107.5, 112.3, 113.9, 115.7, 121.6, 123.0, 125.2, 128.2, 136.6, 151.7, 155.3, 157.1, 159.7, 161.1, 168.0; IR: ν 3377, 2360, 1720, 1620, 1203, 735 cm$^{-1}$. HRMS (ESI) for C$_{26}$H$_{24}$NaO$_7$ (M+Na), (Calc.) 471.1414, found 471.1413. All spectroscopic data are in accordance with literature.[5]

Procedure for the Preparation of 11:

To a 25 mL flask was added 9 (100 mg, 0.35 mmol), phenyl boronic acid (122 mg, 1 mmol), K$_2$CO$_3$ powder (210 mg, 1.7 mmol) and DMF (10 mL). The mixture was degassed three times for a total time of 30 min before Pd(PPh$_3$)$_4$ (19 mg, 0.017 mmol) was added. The flask was degassed again and refilled with argon. The mixture was heated at 75° C. overnight. Water was added and the aqueous solution was extracted with ethyl acetate three times. The organic phases were combined and washed with brine. The organic layer was dried with Na$_2$SO$_4$, concentrated and purified on silica gel to give 11 (98 mg, 0.34 mmol, 97%) as a colorless oil. $^1$H NMR (400 MHz, CDCl$_3$, TMS): δ 3.91 (s, 3H), 4.02 (s, 3H), 7.25 (dd, J=0.8, 2.2 Hz, 1H), 7.38 (t, J=7.4 Hz, 1H), 7.46 (t, J=7.2 Hz, 2H), 7.53 (d, J=0.8 Hz, 1H), 7.59 (d, J=2.3 Hz, 1H), 7.88 (d, J=7.6 Hz, 2H); $^{13}$C NMR (100 MHz, CDCl$_3$): δ 52.1, 56.0, 101.4, 102.2, 112.9, 122.1, 123.6, 124.8, 128.6, 128.8, 130.2, 156.2, 156.7, 157.1, 166.8; IR: ν 2952, 2361, 1716, 1564, 1310, 1131, 735 cm$^1$. HRMS (ESI) for C$_{17}$H$_{14}$NaO$_4$ (M+Na), (Calc.) 305.0784, found 305.0778.

Procedure for the Preparation of 12:

To a solution of 11 (50 mg, 0.177 mmol) in 10 mL of 1,2-dichloroethane was added NBS (62 mg, 0.35 mmol) and 2 mL of DMF. The mixture was stirred at 80° C. for 10 min before the reaction was completed. Saturated Na$_2$S$_2$O$_3$ solution was added to quench the reaction and extracted with ethyl acetate. The combined organic phases were collected, concentrated and purified by flash column chromatography to give bromide 12 (32 mg, 0.089 mmol, 50%) as a colorless oil. $^1$H NMR (400 MHz, CDCl$_3$, TMS): δ 3.89 (s, 3H), 4.00 (s, 3H), 7.16 (d, J=2.3 Hz, 1H), 7.25 (d, J=2.3 Hz, 1H), 7.41 (td, J=1.4, 8.4 Hz, 1H), 7.46-7.50 (m, 2H), 8.08 (td, J=1.7, 7.1 Hz, 2H); $^{13}$C NMR (100 MHz, CDCl$_3$): δ 52.2, 56.0, 92.3, 99.2, 113.5, 119.8, 125.8, 127.3, 128.5, 129.2, 129.4, 151.8, 155.0, 157.8, 167.0; IR: ν 3404, 2924, 2361, 1734, 1374, 1045, 737 cm-1. HRMS (ESI) for C$_{17}$H$_{13}$BrNaO$_4$ (M+Na), (Calc.) 382.9889, found 382.9877.

Procedure for the Preparation of 13:

To a 10 mL flask was added bromide 12 (30 mg, 0.083 mmol), (3,5-dimethoxyphenyl)boronic acid (48 mg, 0.25 mmol), K$_2$CO$_3$ powder (62 mg, 0.4 mmol) and DMF (5 mL). The mixture was degassed three times for a total of 30 min before Pd(PPh$_3$)$_4$ (5 mg, 0.004 mmol) was added. The flask was degassed again and refilled with argon. Then the mixture was heated at 110° C. for 3 h. Water was added and extracted with ethyl acetate for three times. The combined organic phase was washed with brine. The organic layer was dried with Na$_2$SO$_4$, concentrated and purified on silica gel with 10% acetone in hexane as fluent to give 13 (31 mg, 0.074 mmol, 89%) as a colorless oil. $^1$H NMR (400 MHz, CDCl$_3$, TMS): δ 3.24 (s, 3H), 3.76 (s, 6H), 3.90 (s, 3H), 6.51 (s, 3H), 7.23 (d, J=1.9 Hz, 1H), 7.25 (d, J=2.4 Hz, 1H), 7.27-7.31 (m, 3H), 7.54-7.57 (m, 2H); $^{13}$C NMR (100 MHz, CDCl$_3$): δ 51.5, 55.5, 56.1, 99.5, 100.3, 107.4, 112.7, 117.3, 121.4, 125.7, 126.8, 128.3, 128.4, 130.3, 136.3, 151.4, 155.5, 157.5, 161.1, 167.9; IR: ν 3368, 2923, 2360, 1721, 1593, 1134, 693 cm$^{-1}$. HRMS (ESI) for C$_{25}$H$_{22}$NaO$_6$ (M+Na), (Calc.) 441.1309, found 441.1308.

Procedure for the Preparation of 14:

To a solution of 13 (30 mg, 0.071 mmol) in 5 mL of dry dichloromethane was added BBr$_3$ (1.4 mL, 1M in CH$_2$Cl$_2$) dropwise at −78° C. The temperature was allowed warm to room temperature slowly and stirred overnight. After the reaction was completed, the flask was cooled down to −78° C. again and saturated NaHCO$_3$ solution was added slowly to quench the reaction. The mixture was filtered and washed with CH$_2$Cl$_2$ and water. The filtrate was collected and purified on silica gel (dichloromethane:acetone:methanol=60:10:1) to give compound 14 (21 mg, 0.061 mmol, 86%) as a yellow solid. m.p.>260° C. $^1$H NMR (500 MHz, DMSO-d6, TMS): δ 6.36 (d, J=1.8 Hz, 1H), 7.13 (d, J=1.8 Hz, 1H), 7.44 (dd, J=1.3, 11.7 Hz, 2H), 7.69-7.74 (m, 3H), 7.96 (dd, J=1.5, 6.3 Hz, 2H) 10.34 (s, 1H), 10.87 (s, 1H); $^{13}$C NMR (125 MHz, DMSO-d6): δ 102.5, 103.2, 104.2, 107.7, 109.0, 110.4, 123.0, 124.6, 128.8, 129.2, 129.9, 130.7, 133.7, 152.8, 155.0, 157.8, 164.1, 166.7, 186.3; IR: ν 3390, 2922, 2361, 1699, 1423, 1238, 1066 cm$^{-1}$. HRMS (ESI) for C$_{21}$H$_{12}$NaO$_5$ (M+Na), (Calc.) 367.0577, found 367.0574.

Procedure for the Preparation of 15:

To a 10 mL flask was added bromide 8 (50 mg, 0.13 mmol), phenylboronic acid (47 mg, 0.39 mmol), K$_2$CO$_3$ powder (90 mg, 0.65 mmol) and DMF (10 mL). The mixture was degassed three times for a total time of 30 min before Pd(PPh$_3$)$_4$ (7 mg, 0.006 mmol) was added. The flask was degassed again and refilled with argon. The mixture was heated at 110° C. for 2 h. Water was added and extracted with ethyl acetate for three times. The organic phase was collected and washed with brine. The organic layer was dried with Na$_2$SO$_4$, concentrated to give crude product (48 mg, 0.124 mmol) as a colorless oil.

To a solution of crude product obtained in the last step (30 mg, 0.077) in 5 mL of dry dichloromethane was added BBr$_3$ (1.5 mL, 1M in CH$_2$Cl$_2$) dropwise at −78° C. The temperature was allowed to warm to room temperature slowly and stirred overnight. After the reaction was completed, the flask was cooled down to −78° C. again and saturated NaHCO$_3$ solution was added slowly to quench the reaction. The mixture was filtered and washed with CH$_2$Cl$_2$ and water. The filtrate was collected and dried under vacuum to give compound 15 (22 mg, 0.067 mmol, 83% for two steps) as a yellow solid. m.p.>260° C. $^1$H NMR (400 MHz, DMSO-d6, TMS): δ 7.03 (d, J=8.6 Hz, 2H), 7.39 (d, J=12.6 Hz, 2H), 7.54 (t, J=7.7 Hz, 1H), 7.67 (t, J=7.0 Hz, 1H), 7.77 (d, J=8.6 Hz, 2H), 8.09 (d, J=8.0 Hz, 1H), 8.34 (d, J=8.0 Hz, 1H), 10.21 (s, 1H), 10.27 (s, 1H); $^{13}$C NMR (100 MHz, DMSO-d6): δ 104.6, 107.6, 107.8, 116.5, 120.9, 124.3, 124.4, 125.4, 128.2, 129.0, 131.1, 131.6, 132.5, 133.3, 153.6, 155.8, 158.0, 160.1, 181.9; IR: νcm$^{-1}$. HRMS (ESI) for C$_{21}$H$_{12}$NaO$_4$ (M+Na), (Calc.) 351.0628, found 351.0618.

Procedure for the Preparation of 16:

To a 10 mL flask was added bromide 8 (30 mg, 0.08 mmol), 3-methoxyphenylboronic acid (36 mg, 0.24 mmol), K$_2$CO$_3$ powder (56 mg, 0.4 mmol) and DMF (3 mL). The mixture was degassed three times for a total time of 30 min before Pd(PPh$_3$)$_4$ (5 mg, 0.004 mmol) was added. The flask was degassed again and refilled with argon. The mixture was heated at 110° C. for 3 h. Water was added and extracted with ethyl acetate for three times. The organic phases were combined and washed with brine. The organic layer was dried with Na$_2$SO$_4$, concentrated and purified on silica gel with 10% acetone in hexane as fluent to give 16 (31 mg, 0.074 mmol, 93%) as a colorless oil. $^1$H NMR (400 MHz, CDCl$_3$, TMS): δ 3.16 (s, 3H), 3.78 (s, 3H), 3.79 (s, 3H), 3.90 (s, 3H), 6.79 (d, J=9.2 Hz, 2H), 6.87 (dd, J=1.5, 2.1 Hz, 1H), 6.92 (d, J=2.0 Hz, 1H), 6.93-6.95 (m, 1H), 7.22 (d, J=2.4 Hz, 1H), 7.25 (d, J=2.4 Hz, 1H), 7.33 (td, J=7.8, 0.3 Hz, 1H), 7.42 (d, J=9.2 Hz, 2H); $^{13}$C NMR (100 MHz, CDCl$_3$): δ 51.4, 55.26, 55.34, 56.1, 99.7, 112.5, 113.5, 113.9, 114.7, 115.8, 121.8, 122.3, 123.1, 125.1, 128.2, 129.7, 136.1, 151.8, 155.3, 157.1, 159.6, 160.0, 167.8; IR: ν 3368, 2922, 2852, 1717, 1247, 832 cm$^{-1}$. HRMS (ESI) for C$_{25}$H$_{22}$NaO$_6$ (M+Na), (Calc.) 441.1309, found 441.1308.

Procedure for the Preparation of 17 and 18:

To a solution of 16 (65 mg, 0.15 mmol) in 15 mL of dry dichloromethane was added BBr$_3$ (3.0 mL, 1M in CH$_2$Cl$_2$) dropwise at −78° C. The temperature was allowed to warm to room temperature slowly and stirred overnight. After the reaction was completed, the flask was cooled down to −78° C. again and saturated NaHCO$_3$ solution was added slowly to quench the reaction. The mixture was filtered and washed with CH$_2$Cl$_2$ and water. The filtrate was collected and purified on silica gel (dichloromethane:acetone:methanol=60:10:1) to give compound 17 (35 mg, 0.102 mmol, 68%) and compound 18 (14 mg, 0.04 mmol, 27%) as yellow solids.

17, m.p.>260° C. $^1$H NMR (500 MHz, acetone-d6, TMS): δ 7.01 (dd, J=1.9, 7.0 Hz, 1H), 7.12 (d, J=7.0 Hz, 2H), 7.33 (d, J=1.6 Hz, 1H), 7.53 (d, J=1.3 Hz, 1H), 7.63 (d, J=1.9 Hz, 1H), 7.83 (d, J=7.0 Hz, 2H), 8.33 (d, J=7.0 Hz, 1H); $^{13}$C NMR (125 MHz, acetone-d6): δ 103.9, 108.3, 108.9, 110.3, 116.7, 116.9, 122.7, 125.6, 126.9, 127.0, 131.6, 132.2, 134.7, 154.5, 156.2, 158.3, 160.3, 162.2, 181.8; IR: ν 3365, 2925, 2360, 2125, 1641, 1370, 1238 cm$^{-1}$. HRMS (ESI) for C$_{21}$H$_{12}$NaO$_5$ (M+Na), (Calc.) 367.0577, found 367.0573.

18, m.p.>260° C. $^1$H NMR (500 MHz, DMSO-d6, TMS): δ 6.94 (dd, J=1.2, 8.0 Hz, 1H), 7.02 (d, J=9.1 Hz, 2H), 7.43 (q, J=1.8 Hz, 2H), 7.58 (t, J=8.0 Hz, 1H), 7.63 (dd, J=1.2, 8.0 Hz, 1H), 7.78 (d, J=9.1 Hz, 2H), 10.30 (s, 2H), 13.82 (s, 1H); $^{13}$C NMR (125 MHz, DMSO-d6): δ 105.0, 107.2, 107.5, 114.4, 116.0, 116.3, 116.5, 120.2, 123.8, 124.0, 130.6, 132.3, 135.8, 152.8, 156.7, 157.6, 159.9, 164.1, 188.0; IR: 3369, 2921, 2360, 1695, 1238, 1139, 669 cm$^{-1}$. HRMS (ESI) for C$_{21}$H$_{12}$NaO$_5$ (M+Na), (Calc.) 367.0577, found 367.0574.

Animal Studies:

Methods:

Diptoindonesin G (Dip G) was obtained from the small molecule screening facility. Dip G was prepared by dissolving the stock powder in 100% DMSO to a final concentration of 50 mg/mL. This stock solution was then diluted 1:5 into a 40% polyethylene glycol (PEG 300)/40% normal saline (0.9% NaCl) solution to a final concentration of 20% Dip G solution. Vehicle was prepared identically, substituting DMSO instead of Dip G solution. PEG and saline were filtered at 0.2-0.5 m prior to use to ensure sterility.

Twelve Foxn1-nu homozygous mice were obtained from The Jackson Laboratory (Bar Harbor, Me.). Mice were randomized to control or active treatment prior to estrogen pellet placement. After allowing time for acclimatization, estrogen pellets were surgically inserted into the test mice, subcutaneously on the back. The skin at the site of surgery was prepared by washing with povidone iodine, allowing a three-minute contact time. Surgery was performed in a laminar flow hood while mice were under anesthesia. Incisions of less than 1 cm were made low in the back using a short scissors. Slow-release estrogen pellets (0.05 mg/60 day release) were implanted in each incision. Wounds were sealed with "VETBOND"®-brand surgical adhesive (3M Company, St. Paul, Minn.). At the same time, the mice were injected with $10^7$ T-47D cells (ATCC HTB-133) twice, once in each mammary fat pad underneath the leg with 100 uL of fluid per injection site, using 25G needles.

Mice were monitored twice weekly for weight changes and tumor growth (measured in diameter and volume) with calipers. Following tumors reaching an appropriate size (~5 mm in diameter, taking approximately 3 months after grafting), intra-tumoral injections were begun with vehicle containing 20 mg/kg of Dip G or control vehicle in a total volume of 50 μL split between tumors on each mammary fat pad. Three mice (6 tumors) received control injections and eight (16 tumors) received Dip G. Injections were administered 3 times per week with at least one day of rest between injections, for a total of 10-12 injections. Cohorts were sacrificed by cage individually in numerical order, beginning with the 10$^{th}$ injection and sacrificing one cage per injection for pharmacokinetic time points from that injection onward. In mice with very small tumors, dosing was switched from intra-tumoral to subcutaneous at later time points.

Results:

One mouse was sacrificed prior to dosing due to a C. bovis infection that could not be cleared by antibiotic treatment.

Tumor sizes at baseline ranged for from 23 to 475 mm$^3$, see Table 1, although the 475 mm$^3$ tumor was an outlier.

Injection typically resulted in mild to moderate pain indicated by squinting and hunching, though signs of pain abated within 30 minutes. Injection also typically resulted in swelling of the tumor at the injection site, usually increasing tumor diameter by 0.5-2 mm. Swelling typically abated by 72 hours post-injection. Thus, measurements taken less than 72 hours apart are not considered representative of actual tumor growth.

Mice receiving Dip G compound showed signs of subcutaneous bleeding, bruising, and discoloration around the tumor and the site of injection. This phenomenon was not observed in mice injected with vehicle only. By dose 8, this discoloration was universal among Dip G-treated mice.

A summary of individual tumor measurements by day can be found in Table 1. Both vehicle and Dip G-treated tumors declined in volume with treatment. Control treated tumors (n=6 tumors, 3 mice) were 70% of original size (decreased by 30%) at study completion (95% confidence interval for the mean, 47-92%), while tumors (n=16 tumors, 8 mice) treated with Dip-G were 46% (95% confidence interval for the mean, 25-64%) of original size (decreased by 54%), although this did not quite meet statistical significance (p=0.06). See FIG. 3, which graphically presents the results tabulated in Table 1. Some tumors treated with Dip G resolved to the point of almost being unmeasureable (less than 10 mm$^3$). Such resolution did not occur in the vehicle treated group.

Individual tumors decreasing by 50% of more were categorized as responders. In the control treated tumors (n=6 tumors, 3 mice), only one of six tumors responded (17%) while in mice (n=16 tumors, 8 mice) treated with Dip G, 12 of 16 (75%) responded, p=0.023, Fischer's exact test.

TABLE 1

| | | | Tumor Volumes (mm³) Day | | | | | | | | |
|---|---|---|---|---|---|---|---|---|---|---|---|
| Cage | Mouse | TX | 0 | 3 | 5 | 8 | 10 | 12 | 15 | 19 | 23 |
| 1 | 1 | DIPG | 47.1 | 149.4 | 111.6 | 43.6 | 63.6 | 189.2 | 92.5 | 58.2 | 34.2 |
| 1 | 2 | DIPG | 52.9 | 68.9 | 87.7 | 40.3 | 67.7 | 0.5 | 49.6 | 35.7 | 14.9 |
| 1 | 3 | Control | 59.2 | 82.9 | 92.5 | 59.2 | 68.5 | 68.5 | 74.4 | 80.2 | 48.6 |
| 1 | 4 | DIPG | 75.1 | 113.1 | 100.0 | 74.1 | 106.2 | 225.3 | 81.6 | 91.9 | 0.5 |
| 2 | 5 | DIPG | 40.3 | 29.8 | 34.7 | 20.0 | 73.0 | 33.6 | 41.6 | 38.8 | 12.2 |
| 2 | 6 | DIPG | 39.7 | 71.4 | 36.0 | 26.0 | 39.2 | 34.5 | 35.3 | 12.0 | 9.1 |
| 2 | 7 | Control | 131.0 | 136.9 | 137.2 | 102.6 | 102.9 | 92.3 | 112.9 | 75.6 | 79.3 |
| 3 | 8 | DIPG | 71.3 | 25.7 | 34.7 | 14.5 | 37.6 | 18.5 | 32.0 | 19.7 | 29.7 |
| 3 | 9 | DIPG | 50.8 | 69.6 | 58.8 | 52.9 | 64.8 | 77.2 | 78.0 | 45.6 | 81.5 |
| 3 | 10 | Control | 42.9 | 37.8 | 37.6 | 25.4 | 20.7 | 31.2 | 16.4 | 13.1 | 27.4 |
| 3 | 11 | DIPG | 25.4 | 17.2 | 23.1 | 14.0 | 28.1 | 13.9 | 19.7 | 11.5 | 10.3 |
| 1 | 1 | DIPG | 80.2 | 126.0 | 108.0 | 65.0 | 105.6 | 123.6 | 72.5 | 58.8 | 51.9 |
| 1 | 2 | DIPG | 80.2 | 79.8 | 84.7 | 55.0 | 95.3 | 0.5 | 37.0 | 28.7 | 13.1 |
| 1 | 3 | Control | 475.2 | 404.9 | 393.6 | 380.7 | 456.2 | 410.5 | 447.0 | 423.2 | 461.0 |
| 1 | 4 | DIPG | 96.2 | 144.9 | 152.5 | 99.1 | 123.0 | 97.7 | 62.5 | 90.9 | 7.9 |
| 2 | 5 | DIPG | 24.9 | 40.7 | 51.6 | 32.8 | 49.0 | 48.7 | 22.9 | 15.6 | 9.5 |
| 2 | 6 | DIPG | 71.3 | 43.3 | 44.0 | 46.6 | 56.1 | 49.0 | 35.4 | 24.6 | 28.1 |
| 2 | 7 | Control | 77.2 | 56.4 | 47.1 | 43.7 | 36.0 | 42.5 | 40.0 | 36.1 | 27.4 |
| 3 | 8 | DIPG | 70.2 | 70.7 | 58.8 | 55.2 | 58.2 | 63.6 | 53.0 | 35.7 | 29.8 |
| 3 | 9 | DIPG | 29.6 | 30.8 | 36.1 | 20.7 | 32.9 | 29.4 | 22.0 | 14.9 | 18.5 |
| 3 | 10 | Control | 38.7 | 41.6 | 37.3 | 32.0 | 42.3 | 26.6 | 32.7 | 13.0 | 31.0 |
| 3 | 11 | DIPG | 23.1 | 15.1 | 18.9 | 21.8 | 44.5 | 23.1 | 20.1 | 9.3 | 10.1 |

What is claimed is:

1. A compound selected from the group consisting of:

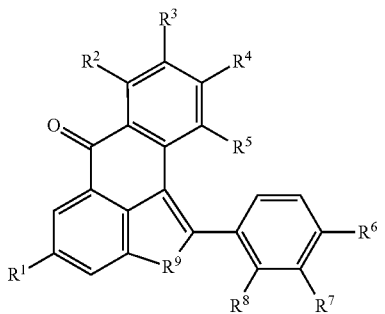

wherein $R^1$, $R^2$, $R^3$, $R^4$, $R^5$, $R^6$, $R^7$, and $R^8$ are independently selected from the group consisting of —H, —OH, —OR$^{10}$, —NH$_2$, —NHR$^{10}$, and —NR$^{10}$R$^{11}$, wherein $R^{10}$ and $R^{11}$ are independently selected from the group consisting of $C_1$-$C_6$-alkyl, provided that $R^1$, $R^2$, and $R^4$ are not simultaneously —OH or —OR$^{10}$; and further provided that at least one of $R^6$, $R^7$, or $R^8$ is —OH;

$R^9$ is —O—, —NH—, or —S—; and salts thereof.

2. The compound of claim 1, wherein the salts are pharmaceutically suitable salts.

3. A compound selected from the group consisting of:

wherein $R^1$, $R^2$, $R^3$, $R^4$, $R^5$, $R^6$, $R^7$, and $R^8$ are independently selected from the group consisting of —H, —OH, —OR$^{10}$, —NH$_2$, —NHR$^{10}$, and —NR$^{10}$R$^{11}$, wherein $R^{10}$ and $R^{11}$ are independently selected from the group consisting of $C_1$-$C_6$-alkyl, provided that $R^1$, $R^2$, and $R^4$ are not simultaneously —OH or —OR$^{10}$, and further provided that at least one of $R^1$, $R^3$, $R^4$, or $R^5$ is —OH, and at least one of $R^6$, $R^7$, or $R^8$ is —OH; and wherein $R^9$ is —O—; and salts thereof.

4. The compound of claim 3, wherein $R^1$ is —OH.
5. The compound of claim 3, wherein $R^2$ is —OH.
6. The compound of claim 3, wherein $R^3$ is —OH.
7. The compound of claim 3, wherein $R^4$ is —OH.
8. The compound of claim 3, wherein $R^5$ is —OH.
9. The compound of claim 3, wherein $R^6$ is —OH.
10. The compound of claim 3, wherein $R^7$ is —OH.
11. The compound of claim 3, wherein $R^8$ is —OH.

12. A compound selected from the group consisting of:

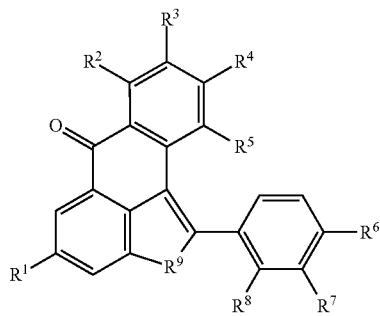

wherein $R^1$, $R^2$, $R^3$, $R^4$, $R^5$, $R^6$, $R^7$, and $R^8$ are independently selected from the group consisting of —H, —OH, —$OR^{10}$, —$NH_2$, —$NHR^{10}$, and —$NR^{10}R^{11}$, provided that at least one of $R^1$, $R^2$, $R^3$, $R^4$, $R^5$ is —OH, and at least one of $R^6$, $R^7$, and $R^8$ is —OH, wherein $R^{10}$ and $R^{11}$ are independently selected from the group consisting of $C_1$-$C_6$-alkyl, and provided that $R^1$, $R^2$, $R^4$, and $R^6$ are not simultaneously —OH;

wherein $R^9$ is —NH—; and salts thereof.

13. The compound of claim 12, wherein $R^1$ is —OH.
14. The compound of claim 12, wherein $R^2$ is —OH.
15. The compound of claim 12, wherein $R^3$ is —OH.
16. The compound of claim 12, wherein $R^4$ is —OH.
17. The compound of claim 12, wherein $R^5$ is —OH.
18. The compound of claim 12, wherein $R^6$ is —OH.
19. The compound of claim 12, wherein $R^7$ is —OH.
20. The compound of claim 12, wherein $R^8$ is —OH.

21. A compound selected from the group consisting of:

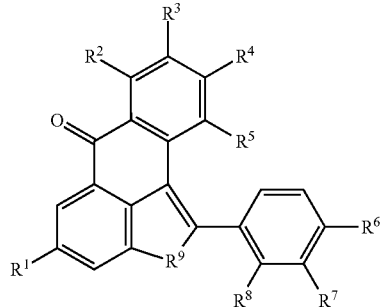

wherein $R^1$, $R^2$, $R^3$, $R^4$, $R^5$, $R^6$, $R^7$, and $R^8$ are independently selected from the group consisting of —H, —OH, —$OR^{10}$, —$NH_2$, —$NHR^{10}$, and —$NR^{10}R^{11}$, wherein $R^{10}$ and $R^{11}$ are independently selected from the group consisting of $C_1$-$C_6$-alkyl, provided that $R^1$, $R^2$, $R^4$, and $R^6$ are not simultaneously —OH; and wherein $R^9$ is —S—; and salts thereof.

22. The compound of claim 21, wherein $R^1$ is —OH.
23. The compound of claim 21, wherein $R^2$ is —OH.
24. The compound of claim 21, wherein $R^3$ is —OH.
25. The compound of claim 21, wherein $R^4$ is —OH.
26. The compound of claim 21, wherein $R^5$ is —OH.
27. The compound of claim 21, wherein $R^6$ is —OH.
28. The compound of claim 21, wherein $R^7$ is —OH.
29. The compound of claim 21, wherein $R^8$ is —OH.

30. A pharmaceutical composition comprising a compound as recited in claim 1, in combination with a pharmaceutically suitable delivery vehicle.

31. A method of inhibiting neoplastic cell growth, the method comprising contacting a neoplastic cell or a cell suspected of being neoplastic with a growth inhibiting-effective amount of a compound as in claim 1.

* * * * *